(12) United States Patent
Sethumadhavan et al.

(10) Patent No.: US 11,995,592 B2
(45) Date of Patent: *May 28, 2024

(54) SYSTEMS AND METHODS FOR ENHANCING WORKFLOW EFFICIENCY IN A HEALTHCARE MANAGEMENT SYSTEM

(71) Applicant: Apixio, LLC, San Mateo, CA (US)

(72) Inventors: Vishnuvyas Sethumadhavan, Mountain View, CA (US); John O. Schneider, Los Gatos, CA (US); Richard Joseph Belcinski, San Jose, CA (US)

(73) Assignee: Apixio, LLC, San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/148,111

(22) Filed: Dec. 29, 2022

(65) Prior Publication Data

US 2023/0143557 A1 May 11, 2023

Related U.S. Application Data

(63) Continuation of application No. 14/829,607, filed on Aug. 18, 2015, now Pat. No. 11,544,652, which is a
(Continued)

(51) Int. Cl.
*G06Q 10/0633* (2023.01)
*G16H 10/60* (2018.01)
(Continued)

(52) U.S. Cl.
CPC ......... *G06Q 10/0633* (2013.01); *G16H 10/60* (2018.01); *G16H 40/20* (2018.01); *G06Q 10/10* (2013.01)

(58) Field of Classification Search
CPC .... G06Q 10/0633; G06Q 50/24; G06Q 50/22; G16H 10/60; G16H 40/20; G06F 19/328
See application file for complete search history.

(56) References Cited

U.S. PATENT DOCUMENTS 5,164,899 A 11/1992 Sobotka et al.
5,307,262 A 4/1994 Ertel
(Continued)

FOREIGN PATENT DOCUMENTS

JP 09135816 A 5/1997
JP H1145304 A 2/1999
(Continued)

OTHER PUBLICATIONS

Lynunn, How Elasticsearch calculates significant terms, Jun. 10, 2015, ComperioSearch (Year: 2015).
(Continued)

*Primary Examiner* — Sheetal R Paulson
*Assistant Examiner* — Chad A Newton
(74) *Attorney, Agent, or Firm* — Armstrong Teasdale LLP

(57) ABSTRACT

To achieve the foregoing and in accordance with the present invention, systems and methods for workflow management are provided. In some embodiments, a set of data elements, which are extracted from medical information, are received. The elements are bundled according to one or more similar attributes to form work items. Work items are bundles of data elements for which value is to be extracted for a particular user objective. Next the workflows are configured according to event history for the work items, current action, and user context. The work items may then be routed through the workflow based upon the work items' "energy". Work item energy is the probability and degree to which a next action taken in a workflow to that particular work item will further a user objective.

20 Claims, 16 Drawing Sheets

Related U.S. Application Data continuation-in-part of application No. 14/720,931, filed on May 25, 2015, now Pat. No. 11,715,569, and a continuation-in-part of application No. 14/709,410, filed on May 11, 2015, now Pat. No. 9,639,662, which is a continuation of application No. 13/783,289, filed on Mar. 2, 2013, now Pat. No. 9,032,513, which is a continuation-in-part of application No. 13/747,336, filed on Jan. 22, 2013, now abandoned, said application No. 14/720,931 is a continuation of application No. 13/730,824, filed on Dec. 28, 2012, now Pat. No. 9,043,901, which is a continuation-in-part of application No. 13/656,652, filed on Oct. 19, 2012, now Pat. No. 8,898,798, which is a continuation-in-part of application No. 13/223,228, filed on Aug. 31, 2011, now Pat. No. 10,176,541, said application No. 13/783,289 is a continuation-in-part of application No. 13/223,228, filed on Aug. 31, 2011, now Pat. No. 10,176,541.

(60) Provisional application No. 62/059,139, filed on Oct. 2, 2014, provisional application No. 61/590,330, filed on Jan. 24, 2012, provisional application No. 61/379,228, filed on Sep. 1, 2010.

(51) Int. Cl.
*G16H 40/20* (2018.01)
*G06Q 10/10* (2023.01)

(56) References Cited

U.S. PATENT DOCUMENTS

| | | |
|---|---|---|
| 5,544,044 A | 8/1996 | Leatherman |
| 5,875,263 A | 2/1999 | Froessl |
| 6,076,088 A | 6/2000 | Paik et al. |
| 6,209,095 B1 | 3/2001 | Anderson et al. |
| 6,266,645 B1 | 7/2001 | Simpson |
| 6,336,108 B1 | 1/2002 | Thiesson et al. |
| 6,341,265 B1 | 1/2002 | Provost et al. |
| 6,505,196 B2 | 1/2003 | Drucker et al. |
| 6,601,055 B1 | 7/2003 | Roberts |
| 6,874,085 B1 | 3/2005 | Koo et al. |
| 7,321,861 B1 | 1/2008 | Oon |
| 7,702,524 B1 | 4/2010 | Whibbs et al. |
| 7,925,678 B2 | 4/2011 | Botros et al. |
| 8,254,681 B1 | 8/2012 | Poncin et al. |
| 8,380,530 B2 | 2/2013 | Marshall |
| 8,620,078 B1 | 12/2013 | Chapleau et al. |
| 8,977,076 B2 | 3/2015 | Samadani et al. |
| 9,495,515 B1 | 11/2016 | Kennedy et al. |
| 10,628,553 B1 | 4/2020 | Murrish |
| 2001/0042080 A1 | 11/2001 | Ross |
| 2002/0007284 A1 | 1/2002 | Schurenberg et al. |
| 2002/0010679 A1 | 1/2002 | Felsher |
| 2002/0103834 A1 | 8/2002 | Thompson et al. |
| 2002/0120466 A1 | 8/2002 | Finn |
| 2002/0143562 A1 | 10/2002 | Lawrence |
| 2002/0188182 A1 | 12/2002 | Haines et al. |
| 2003/0004748 A1 | 1/2003 | Coleman et al. |
| 2003/0046280 A1 | 3/2003 | Rotter et al. |
| 2003/0084043 A1 | 5/2003 | Acharya et al. |
| 2003/0120458 A1 | 6/2003 | Rao |
| 2003/0120640 A1 | 6/2003 | Ohta et al. |
| 2003/0220915 A1 | 11/2003 | Fagan et al. |
| 2003/0229510 A1 | 12/2003 | Kerr |
| 2004/0073458 A1 | 4/2004 | Jensen |
| 2004/0076264 A1 | 4/2004 | Sorenson |
| 2004/0109028 A1 | 6/2004 | Stern et al. |
| 2004/0122702 A1 | 6/2004 | Sabol et al. |
| 2004/0172297 A1 | 9/2004 | Rao et al. |
| 2004/0220895 A1 | 11/2004 | Carus et al. |
| 2004/0249667 A1 | 12/2004 | Oon |
| 2005/0043986 A1 | 2/2005 | McConnell et al. |
| 2005/0137912 A1 | 6/2005 | Rao et al. |
| 2005/0138017 A1 | 6/2005 | Keen et al. |
| 2005/0154690 A1 | 7/2005 | Nitta et al. |
| 2005/0182659 A1 | 8/2005 | Huttin |
| 2005/0192792 A1 | 9/2005 | Carus et al. |
| 2005/0203773 A1 | 9/2005 | Soto et al. |
| 2005/0228593 A1 | 10/2005 | Jones |
| 2005/0240439 A1 | 10/2005 | Covit et al. |
| 2005/0251422 A1 | 11/2005 | Wolfman et al. |
| 2005/0283062 A1 | 12/2005 | Hoffman et al. |
| 2006/0026036 A1 | 2/2006 | Mahmood |
| 2006/0026525 A1 | 2/2006 | Fischer et al. |
| 2006/0036619 A1 | 2/2006 | Fuerst |
| 2006/0047669 A1 | 3/2006 | Durrence |
| 2006/0053098 A1 | 3/2006 | Gardner et al. |
| 2006/0112050 A1 | 5/2006 | Miikkulainen et al. |
| 2006/0129435 A1 | 6/2006 | Smitherman |
| 2006/0179016 A1 | 8/2006 | Forman et al. |
| 2006/0184475 A1 | 8/2006 | Krishnan et al. |
| 2006/0241978 A1 | 10/2006 | Yoshii |
| 2006/0265251 A1 | 11/2006 | Patterson |
| 2006/0265253 A1 | 11/2006 | Rao et al. |
| 2007/0016450 A1 | 1/2007 | Bhora et al. |
| 2007/0055545 A1 | 3/2007 | Maughan et al. |
| 2007/0055552 A1 | 3/2007 | St. Clair et al. |
| 2007/0061348 A1 | 3/2007 | Holland et al. |
| 2007/0061393 A1 | 3/2007 | Moore |
| 2007/0078680 A1 | 4/2007 | Wennberg |
| 2007/0083390 A1 | 4/2007 | Gorup et al. |
| 2007/0088559 A1 | 4/2007 | Kim |
| 2007/0106754 A1 | 5/2007 | Moore |
| 2007/0118399 A1 | 5/2007 | Avinash |
| 2007/0162308 A1 | 7/2007 | Peters |
| 2007/0168461 A1 | 7/2007 | Moore |
| 2007/0192143 A1 | 8/2007 | Krishnan et al. |
| 2007/0219829 A1 | 9/2007 | Kay |
| 2007/0226211 A1 | 9/2007 | Heinze et al. |
| 2008/0040151 A1 | 2/2008 | Moore |
| 2008/0052255 A1 | 2/2008 | Fan et al. |
| 2008/0077443 A1 | 3/2008 | Singer |
| 2008/0091633 A1 | 4/2008 | Rappaport |
| 2008/0097936 A1 | 4/2008 | Schmidtler et al. |
| 2008/0103828 A1 | 5/2008 | Squilla et al. |
| 2008/0120296 A1 | 5/2008 | Kariathungal |
| 2008/0147441 A1 | 6/2008 | Kil |
| 2008/0195570 A1 | 8/2008 | Alsafadi et al. |
| 2008/0208630 A1 | 8/2008 | Fors et al. |
| 2008/0250025 A1 | 10/2008 | Abhyanker |
| 2008/0256181 A1 | 10/2008 | Morita et al. |
| 2008/0263048 A1 | 10/2008 | Wise |
| 2008/0270120 A1 | 10/2008 | Pestian et al. |
| 2008/0270340 A1 | 10/2008 | Abrams |
| 2008/0287746 A1 | 11/2008 | Reisman |
| 2008/0288292 A1 | 11/2008 | Bi et al. |
| 2008/0320029 A1 | 12/2008 | Stivoric |
| 2009/0024615 A1 | 1/2009 | Pedro |
| 2009/0048877 A1 | 2/2009 | Binns et al. |
| 2009/0070103 A1 | 3/2009 | Beggelman |
| 2009/0076839 A1 | 3/2009 | Abraham-Fuchs et al. |
| 2009/0099876 A1 | 4/2009 | Whitman |
| 2009/0110287 A1 | 4/2009 | Bates et al. |
| 2009/0112882 A1 | 4/2009 | Maresh |
| 2009/0125246 A1 | 5/2009 | Ruiz Laza |
| 2009/0136102 A1 | 5/2009 | Kimpe |
| 2009/0138287 A1 | 5/2009 | Hermann, Jr. |
| 2009/0144082 A1* | 6/2009 | Selbst .............. G06Q 40/02 705/2 |
| 2009/0198517 A1 | 8/2009 | Ruben et al. |
| 2009/0216696 A1 | 8/2009 | Downs et al. |
| 2009/0220175 A1 | 9/2009 | Tzadok et al. |
| 2009/0228303 A1 | 9/2009 | Faulkner et al. |
| 2009/0228909 A1 | 9/2009 | Huang |
| 2009/0238625 A1 | 9/2009 | Ming et al. |
| 2009/0259487 A1 | 10/2009 | Rao et al. |
| 2009/0265189 A1 | 10/2009 | Bartholomew et al. |
| 2009/0271221 A1 | 10/2009 | Aridi |
| 2009/0287504 A1 | 11/2009 | Benjamin et al. |
| 2009/0326981 A1 | 12/2009 | Karkanias et al. |

(56) References Cited

U.S. PATENT DOCUMENTS

| | | |
|---|---|---|
| 2010/0036680 A1 | 2/2010 | Familant |
| 2010/0088107 A1 | 4/2010 | Ur et al. |
| 2010/0117799 A1 | 5/2010 | Dormer |
| 2010/0131299 A1 | 5/2010 | Hasan |
| 2010/0131438 A1 | 5/2010 | Pandya et al. |
| 2010/0131482 A1 | 5/2010 | Linthicum et al. |
| 2010/0145723 A1 | 6/2010 | Hudson et al. |
| 2010/0169123 A1 | 7/2010 | Maus |
| 2010/0174579 A1 | 7/2010 | Hughes |
| 2010/0179827 A1 | 7/2010 | McCallie, Jr. et al. |
| 2010/0185496 A1 | 7/2010 | Hahn |
| 2010/0228721 A1 | 9/2010 | Mok et al. |
| 2010/0274584 A1 | 10/2010 | Kim |
| 2010/0281036 A1 | 11/2010 | Inoue et al. |
| 2010/0310172 A1 | 12/2010 | Natarajan et al. |
| 2010/0324927 A1 | 12/2010 | Tinsley |
| 2010/0324936 A1 | 12/2010 | Vishnubhatla |
| 2011/0004588 A1 | 1/2011 | Leitersdorf et al. |
| 2011/0072002 A1 | 3/2011 | Kirkby et al. |
| 2011/0077972 A1 | 3/2011 | Breitenstein et al. |
| 2011/0078145 A1 | 3/2011 | Chung et al. |
| 2011/0093293 A1 | 4/2011 | G. N. et al. |
| 2011/0093334 A1 | 4/2011 | Wood |
| 2011/0117799 A1 | 5/2011 | Harada et al. |
| 2011/0119089 A1 | 5/2011 | Carlisle |
| 2011/0131062 A1 | 6/2011 | Menschik |
| 2011/0196702 A1 | 8/2011 | Salouk et al. |
| 2011/0225001 A1 | 9/2011 | Shen |
| 2011/0251989 A1 | 10/2011 | Kraaij et al. |
| 2011/0258001 A1 | 10/2011 | Green et al. |
| 2011/0264665 A1 | 10/2011 | Mital et al. |
| 2011/0270632 A1 | 11/2011 | Manning et al. |
| 2011/0295775 A1 | 12/2011 | Wang |
| 2012/0041772 A1 | 2/2012 | Ebadollahi et al. |
| 2012/0060216 A1 | 3/2012 | Chaudhri et al. |
| 2012/0066017 A1 | 3/2012 | Siegel |
| 2012/0089412 A1 | 4/2012 | Bardy et al. |
| 2012/0089606 A1 | 4/2012 | Eshwar et al. |
| 2012/0110016 A1 | 5/2012 | Phillips |
| 2012/0166212 A1 | 6/2012 | Campbell |
| 2012/0215578 A1 | 8/2012 | Frank et al. |
| 2012/0239671 A1 | 9/2012 | Chaudhri et al. |
| 2012/0278102 A1 | 11/2012 | Johnson |
| 2012/0284056 A1 | 11/2012 | Hofstetter |
| 2012/0303378 A1 | 11/2012 | Lieberman |
| 2013/0007020 A1 | 1/2013 | Basu et al. |
| 2013/0046529 A1 | 2/2013 | Grain et al. |
| 2013/0124523 A1 | 5/2013 | Rogers et al. |
| 2013/0159023 A1 | 6/2013 | Srinivas et al. |
| 2013/0231956 A1 | 9/2013 | Chaudhri et al. |
| 2013/0238349 A1 | 9/2013 | Sethumadhavan et al. |
| 2013/0291060 A1 | 10/2013 | Moore |
| 2013/0297536 A1 | 11/2013 | Almosni et al. |
| 2013/0332194 A1 | 12/2013 | DAuria et al. |
| 2013/0332199 A1 | 12/2013 | Freiwat et al. |
| 2014/0012738 A1 | 1/2014 | Woo |
| 2014/0046697 A1 | 2/2014 | Rogers et al. |
| 2014/0136559 A1 | 5/2014 | Kottaram |
| 2014/0257842 A1 | 9/2014 | Heinze et al. |
| 2014/0278832 A1 | 9/2014 | Glavina et al. |
| 2015/0019463 A1 | 1/2015 | Simard et al. |
| 2015/0066537 A1 | 3/2015 | Sheffer et al. |
| 2015/0066539 A1 | 3/2015 | Sheffer et al. |
| 2016/0048643 A1 | 2/2016 | Woods et al. |
| 2017/0132314 A1 | 5/2017 | Liu et al. |

FOREIGN PATENT DOCUMENTS

| | | |
|---|---|---|
| JP | 11219403 A | 8/1999 |
| JP | 2001290890 A | 10/2001 |
| JP | 2001325290 A | 11/2001 |
| JP | 2002318820 A | 10/2002 |
| JP | 2003263507 A | 9/2003 |
| JP | 2004280807 A | 10/2004 |
| JP | 2005309666 A | 11/2005 |
| JP | 2006107299 A | 4/2006 |
| JP | 2006164234 A | 6/2006 |
| JP | 2007193399 A | 8/2007 |
| JP | 2007323525 A | 12/2007 |
| JP | 2008204378 A | 9/2008 |
| JP | 2009193157 A | 8/2009 |
| JP | 4471736 B2 | 6/2010 |
| JP | 2010134946 A | 6/2010 |
| KR | 100750071 B1 | 8/2007 |
| KR | 1020090050881 A | 5/2009 |
| KR | 1020120004749 A | 1/2012 |
| WO | 2008039880 A2 | 4/2008 |

OTHER PUBLICATIONS

Bentkus et al., "Confidence Bounds for a Parameter" Sep. 2001 Mathematics Subject Classification.

Feature Selection, Apr. 5, 2016, Wikipedia (Year: 2016).

Lemeshow et al, Searching one or two databases was insufficient for meta-analysis of observational studies, 7 pages (Year: 2005).

Natarajan et al., "An Analysis of Clinical Queries in an Electronic Health Record Search Utility" Int. J Med Inforamtics, Jul. 2010.

Rector et al., "Medical-Concept Models and Medical Records: An approach based on GALEN adn PEN PAD" Journal of the American Medical Informatics Association, vol. 2 No. 1 Jan./Feb. 1995.

Roque et al., "Using Electronic Patient Records to Discover Disease Correlations and Stratify Patient Cohorts" PLoS Computational Biology, Aug. 2011, vol. 7, Issue 8 el 002141.

The Statistics Calculator, StatPac; Dec. 17, 2003, available from: http:/web.archive.org/web/20031217141819/http://statpac.com/statisticscalculator/percents.htm.

Mori et al., "What is Mash-up?", A Web 2.0 service construction technique, iNTERNET magazine, Impress Corporation, Apr. 1, 2006, No. 135, with English Translation, 54 pages.

Woods Mush-up What is Mash-up besides Yoichi? A Web 2.0 service construction way, iNTERNET magazine make innovation with technology!, JP,Impress Corporation, Apr. 1, 2006, No. 135, p. 30-55,.

\* cited by examiner

SYSTEMS AND METHODS FOR ENHANCING WORKFLOW EFFICIENCY IN A HEALTHCARE MANAGEMENT SYSTEM

CROSS REFERENCE TO RELATED APPLICATIONS

This application is a continuation of and claims priority to U.S. patent application Ser. No. 14/829,607, filed Aug. 18, 2015, which claims the benefit of U.S. Provisional Patent Application No. 62/059,139, filed Oct. 2, 2014.

U.S. patent application Ser. No. 14/829,607 additionally claims the benefit of and is a continuation-in-part of U.S. patent application Ser. No. 14/709,410 filed May 11, 2015, now U.S. Pat. No. 9,639,662, which is a continuation of U.S. patent application Ser. No. 13/783,289, filed Mar. 2, 2013, now U.S. Pat. No. 9,032,513, which is a continuation-in-part of U.S. patent application Ser. No. 13/223,228 filed Aug. 31, 2011, now U.S. Pat. No. 10,176,541, which claims priority to U.S. Provisional Patent Application No. 61/379,228, filed Sep. 1, 2010, and is also a continuation-in-part of U.S. patent application Ser. No. 13/747,336, filed Jan. 22, 2013, which claims priority to U.S. Provisional Application No. 61/590,330, filed Jan. 24, 2012.

U.S. patent application Ser. No. 14/829,607 additionally claims the benefit of and is a continuation-in-part of U.S. patent application Ser. No. 14/720,931, filed May 25, 2015, which is a continuation of U.S. patent application Ser. No. 13/730,824, filed Dec. 28, 2012, now U.S. Pat. No. 9,043,901, which is a continuation-in-part of U.S. patent application Ser. No. 13/656,652, filed Oct. 19, 2012, now U.S. Pat. No. 8,898,798, which claims priority to and is a continuation-in-part of U.S. patent application Ser. No. 13/223,228, filed on Aug. 31, 2011.

All above-referenced applications/patents listed above are hereby fully incorporated in their entirety by this reference.

BACKGROUND

The present invention relates generally to systems and methods for improvements in workflow management in a healthcare system. In particular the presently disclosed systems and methods enable contextual bundling of data into discrete work items, contextual workflow configuration, and efficient energy based routing of the work items in order to maximize a given objective. Some embodiments of the present systems and methods enable more accurate and rapid capture of MediCare eligible conditions, and more valuable and frequent reimbursements for these conditions.

Despite rapid growth of innovation in other fields in recent decades, the world of medical information, including patient medical records, billing, MediCare reimbursements, and a host of other information, has enjoyed little to no useful consolidation, reliability, or ease-of-access, leaving medical professionals, hospitals, clinics, and even insurance companies with many issues, such as unreliability of medical information, uncertainty of diagnosis, lack of standard, under compensation for legitimate MediCare conditions, and a slew of other related problems.

One common problem with the analysis of medical records is that identification of clinically pertinent conditions is often not properly identified, and further, even when identified, the evidence in the patient records to support such a finding is not always properly referenced. Moreover, the process for verifying a condition is often time consuming and labor intensive. This results in a few issues, including: MediCare compensation difficulties, missing of important health conditions and/or misdiagnosis, and lastly the clouding of medical analytics with incomplete or incorrect data.

The first issue, compensation by MediCare, results in providers being underpaid for work performed. This may cause many providers to shy away from MediCare patients, increases cost on other patients, and generally leads to inefficiencies in the administration of government backed medical coverage. Additionally, miss-coding of MediCare claim opens providers to potential audit risk.

The second issue, improper or incomplete diagnosis, can be extremely detrimental to the patient. Often early treatment of a condition results in a far better prognosis for the patient. In the extreme, delays of treatment may reduce the patient's life expectancy. As such, there is a very compelling reason to ensure the medical information of a patient is properly documented, with a high degree of accuracy.

In addition to these direct health impacts to the patient, improper or incomplete diagnosis of the patient can lead to unnecessary tests or follow-ups, which can be financially taxing as well as a drain on the resources of the medical community. Thus there are also tangible financial implications to proper diagnosis with supporting evidence.

Lastly, incorrect or missing data may result in the skewing of analytics performed using the medical records. The medical community is entering into an age of big data analysis. These analyses of large data sets of aggregated medical records generated best practices and means for refining a medical practice. It also enables early detection of health trends and patient behavior. Using these results, medical professionals have the opportunity to greatly increase the efficiency of the administration of medical services. This translates directly into improved patient care at reduced costs. However, such analysis relies upon datasets that are accurate. When the input data is flawed, or incomplete, the analysis suffers.

It is therefore apparent that an urgent need exists for improved workflow management within a medical information system. In particular, the ability to contextually bundle data elements into work items, and contextually configure workflows enables users of such a system significant flexibility in their ability to identify patients with specific diagnosed ailments, enhanced coder efficiency, and larger reimbursements from MediCare or other insurer. In addition to the ability to bundle and configure workflows, the presently disclosed systems and methods enable 'energy based routing' of the work items in order to maximize a user's objective. Thus, not only are the workflows and items contextually pertinent, the actual completion of the actions is completed at maximum efficiency.

SUMMARY

To achieve the foregoing and in accordance with the present invention, systems and methods for workflow management are provided. Such systems and methods enable the configuration of workflows, bundling of work items for processing by the workflows, and energy based routing of work items through the workflows in order to improve the efficiency of healthcare management.

In some embodiments, a set of data elements, which are extracted from medical information, are received. Medical information may include medical records, patient entered information, care team entered information, healthcare device generated information, and billing information. The elements are bundled according to one or more similar attributes to form work items. Work items are bundles of data elements for which value is to be extracted for a particular user objective Next the workflows are configured according to event history for the work items, current action, and user context. The work items may then be routed through the workflow based upon the work items' "energy". Work item energy is the probability and degree to which a next action taken in a workflow to that particular work item will further a user objective. The routing is either exploration or exploitation based upon confidence in a probabilistic model for workflow action outcomes. The exploration routing collects results from processing of work items through a given workflow action in order to tune the probabilistic model. Conversely, the exploitation routing compares an expected outcome for the processing of each work item through the workflow versus a user objective and selects work items that maximize the objective.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which.

DETAILED DESCRIPTION

Figure 1:
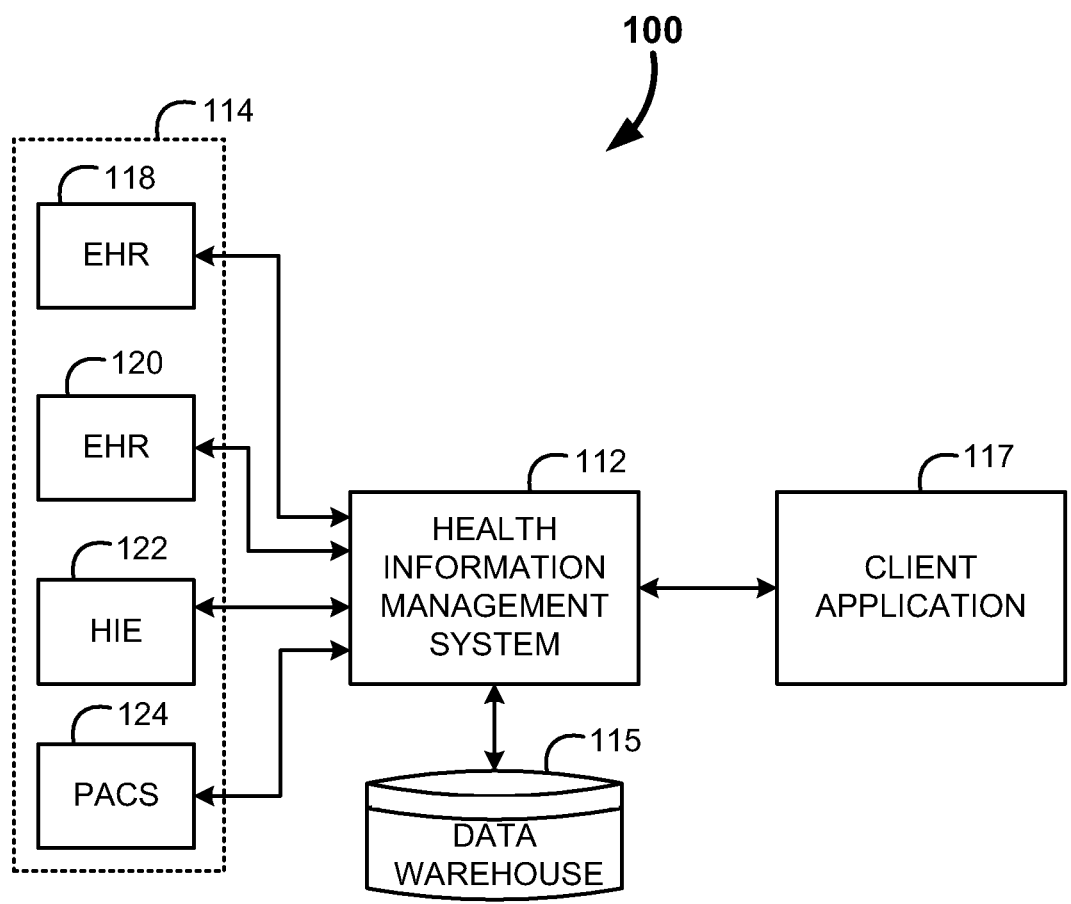
FIG. 1 shows a medical system, in accordance with an embodiment.

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "will," "will not," "shall," "shall not," "must," "must not," "first," "initially," "next," "subsequently," "before," "after," "lastly," and "finally," are not meant to limit the scope of the present invention as the embodiments disclosed herein are merely exemplary Note that the following disclosure includes a series of subsections to aid the clarity of the following disclosure. Such subsections are not intended to artificially limit the scope of the disclosure. As such, any disclosure in a particular subsection may be equally applicable to another section as is applicable.

The present systems and methods are related to efficient generation of "work items." Work items, in the context of this disclosure, are contextual groupings of data elements that are entered into the medical information system. These data elements include givens and predictions from the health care management system, including medical records. The data elements and are grouped according to contextually driven similarities in order to generate the work items. Work items, in the most abstract sense, are things that one hopes to extract value from.

These work items are then processed through a workflow based upon their 'energy'. Energy based routing is performed by identifying the objective of the workflow, and determining what order the work items should be processed through the workflow in order to reach the objective in an efficient way. The workflow itself is configured utilizing state machines in response to context of the workflow, prior actions taken, the user of the workflow, and the work items being processed.

In this manner bundling, contextual configuration of workflows, and energy based routing ensures that a given objective may be efficiently managed within a very large data set. This has particular utility within a healthcare management system where there is a large number of medical records and additional data elements corresponding to patients.

I. Medical Systems

Referring now to FIG. 1, a medical system 100 is shown, in accordance with some embodiments. The system 100 is shown to include medical information sources 114, a health information management system 112, and medical information consumers/client applications (also referred to herein as "output" or "medical output") 117. The medical sources 114 are shown to include one or more electronic health record (EHR) 118, EHR 120, health information exchange (HIE) 122, and a picture archiving and communication system (PACS) 124, among other known sources of medical information.

"Medical information", as used herein, may refer to any health-related information, including but not limited to patient medical records, patient entered information, care team entered information, healthcare device generated information, and billing information. All this medical information, and data elements extracted from this information, are all the raw information utilized in bundling to generate the work items.

The sources 114 generally provides various medical information to the health information management system 112. For example, the EHRs 118 and 120 each may provide information such as medical records and billing, the HIE 122 may provide information such as medical records, and the PACS 124 may provide information such as diagnostic imaging and reports.

The medical information consumers/client applications 117, which may be made of a host of entities or individuals, such as patients, clinics, medical institutions, health organization, and any other medical-related party, use information that is provided by the health information management system 112. For example, user-customized processed medical information is provided by the health information management system 112 to a number of client applications 117. In this case, the health information management system 112 generates user-customized processed medical information to a plurality of users, with at least a portion of the user-customize processed medical information being provided to each of the users based on the relevancy of the portion being provided of each user's specific function or role and each user's associated security privileges.

In some embodiments, the health information management system may merely be a repository of health records and information. In alternate embodiments, the health information management system 112 may have sophisticated capabilities which enable it to index, map, and consolidate medical information, received from the sources 114, and also potentially enabling the tagging of this information, and reconciliation of the tagged information. Indexing, at least in part, processes document and converts them into formats that allows for quick searching across a large collection of documents.

In some methods and embodiments, information that is extracted from the medical data may be bundled into contextual groupings in order to make work items. The medical system may also have workflow configuration abilities that enable workflows to be contextually configured. Lastly, the medical system may include an energy based router that processes work items through the workflows in order to maximize an objective. In some embodiments, the information in the health information management system 112 is encrypted and secure to ensure privacy of sensitive medical information.

It is understood that the sources 114 of FIG. 1 includes merely some examples of the sources that communicate with the health information management system 112 and that other sources, known to those in the field, are contemplated. Similarly, the output 117 may be used by those or entities not discussed herein but that are contemplated and within the scope and spirit of the invention.

Figure 2:
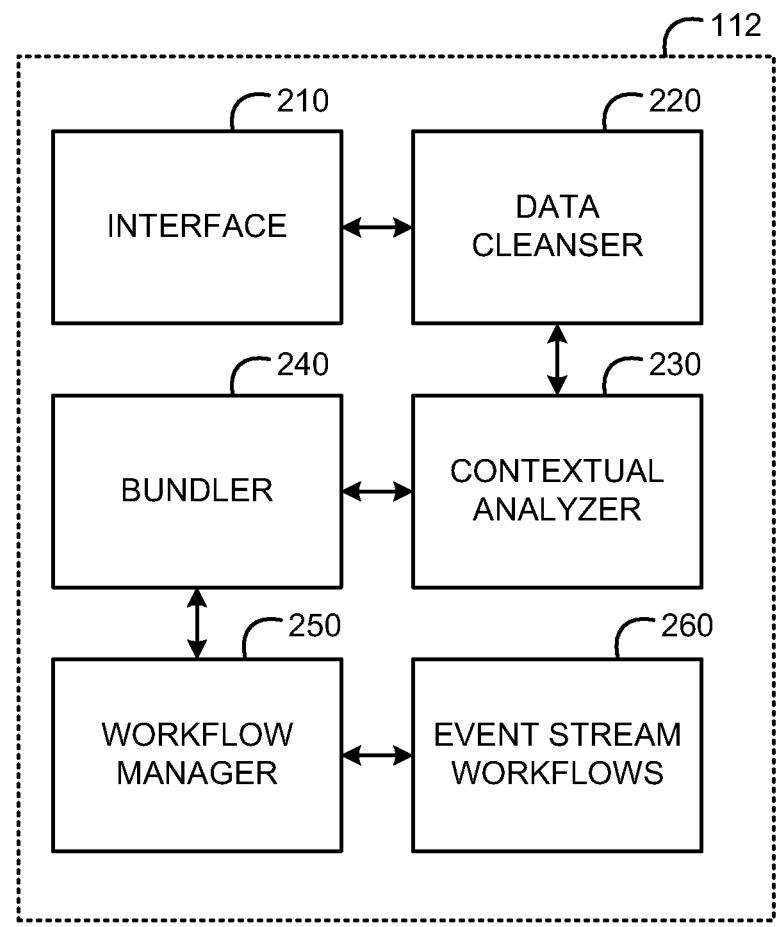
FIG. 2 shows further details of the medical system including the bundler and workflow manager, in accordance with an embodiment.

Turning to FIG. 2, a more detailed illustration for the health information management system 112 is provided. In this example diagram, raw patient objects are received from the plurality of sources 114. The health information management system 112 includes an interface 210 which can collect these objects. These objects may be collected in various forms, such as but not limited to text, html, CCD, CCR, HL7 and any other type or formatted information. The interface 210 then provides to the information to a data cleanser 220 which includes functionality for quality checking and error corrector, in some embodiments.

The quality checking and error corrector may simply delete duplicate errors and redundant patient medical records, such as, multiple records for the same individual appearing as though the records are for different individuals, or multiple data elements that are recorded similarly but slightly differently in the different sources. The quality checking and error corrector may also perform other basic and known error correction processes. Alternatively, more advanced quality checking and error corrector systems may check the quality of medical information provided by various sources 114 by the patients, structured data, and unstructured data, in a Wiki-like mannered setting whereby the users can help maintain and improve the quality of information displayed.

In some embodiments, a contextual analyzer 230 may perform additional analysis of the cleansed data in order to generate a more machine readable dataset. The contextual analyzer 230 may include an indexing and Meta tagging module which may utilize a processor to processing the data, such as indexing and semantic meta-tagging. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others.

After the indexing and meta tagging, a bundler 240 may take the data elements and cluster them according to a context driven by the user of the system. The output of this clustering is a series of work items, which are things for which value may be extracted from. In the context of medical information systems, an example of the work items that are generated are clusters of medical records pertaining to a single patient and a given disease state.

Figure 3:
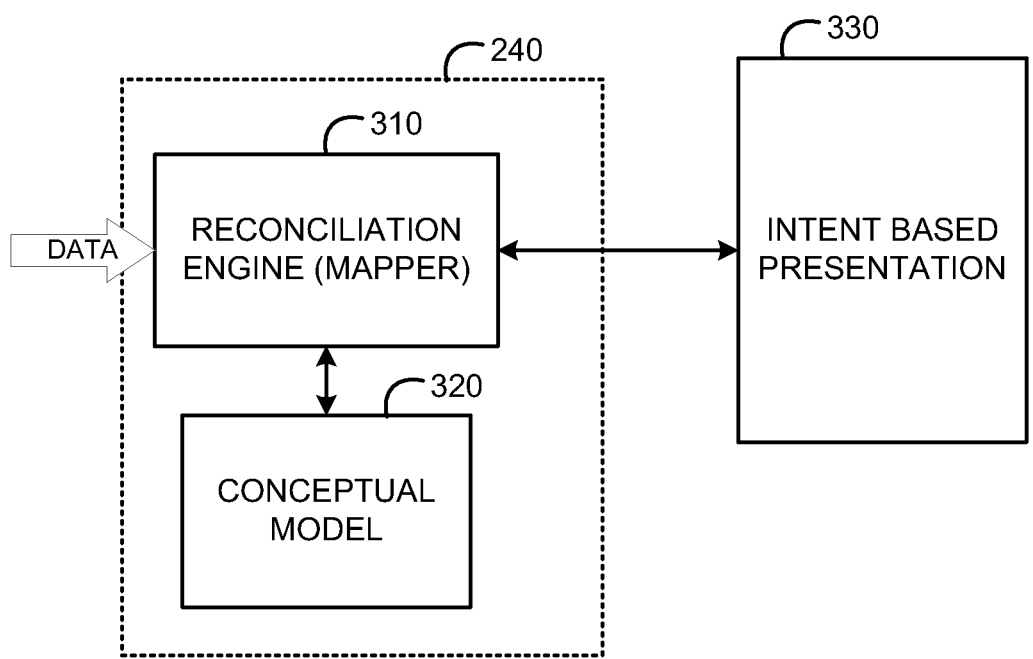
FIG. 3 shows an example embodiment of the bundler, in accordance with an embodiment.

FIG. 3 shows further details of the bundler 240, in accordance with an embodiment of the invention. The bundler 240 is shown to include a reconciliation engine (also referred to hereinafter as the "mapper") 310 responsive to data, which is, at least in part, within the source 114, and is shown to provide reconciled information that is provided to the intent-based presentation block 330.

The engine 310 advantageously learns, through history, ontology, user-input, the type of user, and a host of other factors, similarities between various information from the data, defines characteristics thereof, models this information conceptually, pre-selects and sorts information before providing it the block 330 for presentation in the form of a display, or other known types of presentations. Such processing entails the use of various sets of rules, at various stages, as will be evident shortly relative to subsequent figures and discussions.

Presentation by the block 330 is intent-based, that is, the user of the bundler 240 along with history, and other factors are used to determine the information to be presented. With time, as the engine's 310 knowledge of medical information, such as drugs, type of users, diagnosis, the relationship between various diagnosis/diseases relative to each other and relative to various medications, and other information, increases, the information presented by 330 becomes increasingly intent-based. The information presented at 330 are also known as work items, and are thing from which value may be extracted from. The engine 310 is shown to include a conceptual model block 320, which conceptually models the data, such as to determine similarities.

Figure 4:
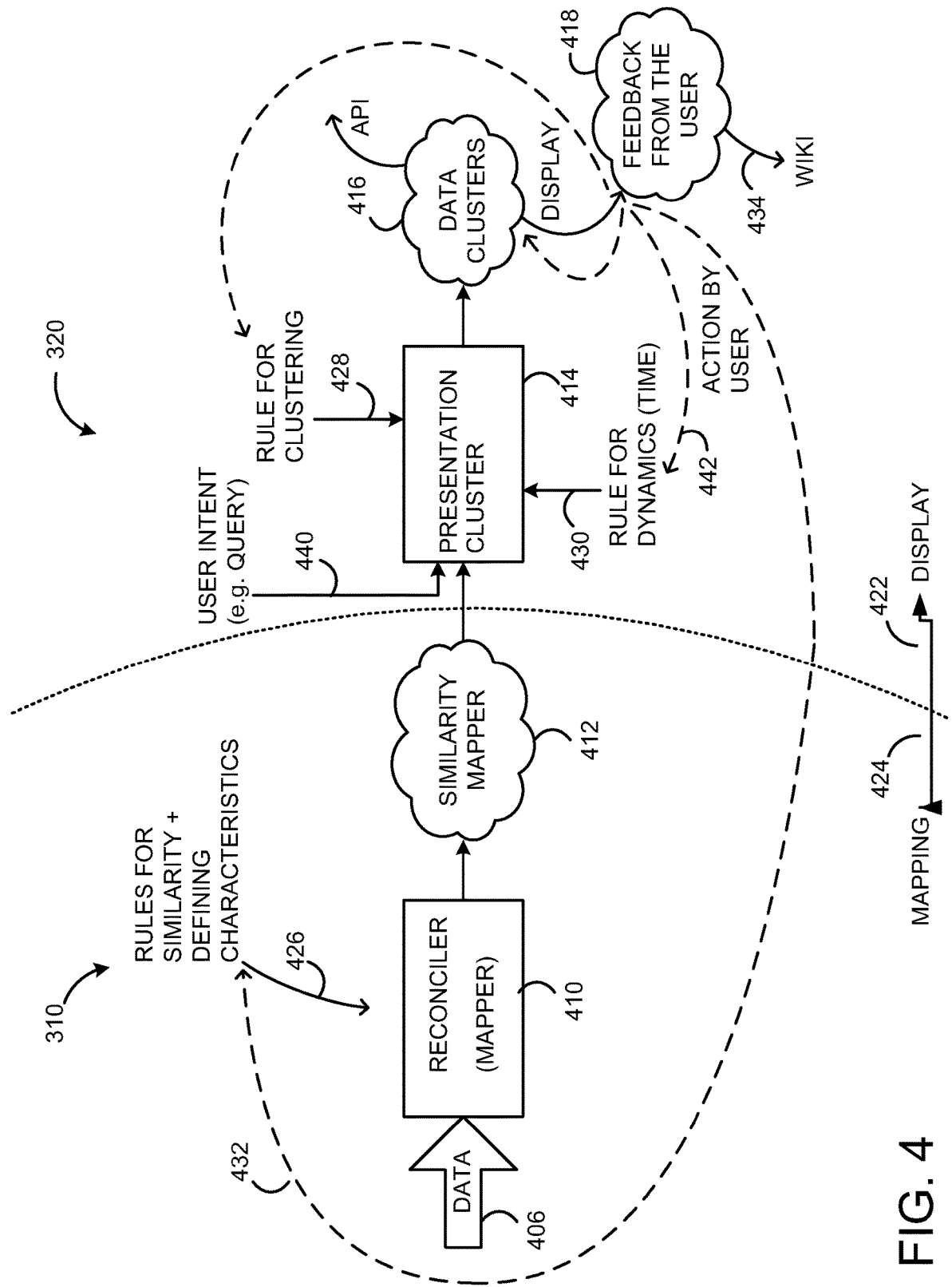
FIG. 4 shows an example diagram of data clustering by the bundler, in accordance with an embodiment.

FIG. 4 shows further details of the engine 310 and the block 320 of FIG. 3. The engine 310 is shown to include a reconciler block 410 that receives data 406 and a similarity mapper 412. The block 320 is shown to include a presentation cluster block 414, which is shown to receive information from the mapper 412.

A set of similarity rules 426, which identify similarities of various types of information, and define characteristics thereof, is shown being utilized by the reconciler 410. The rules 426 are applied to the data 406 to identify similar concepts, which unlike prior art techniques, is not to look for matches and rather to correlate information based on concepts. Through feedback from users 432, this becomes a learned process with improved and more sophisticated conceptual similarity detection. The similarity mapper 412 maps the reconciled information, generated by the reconciler 410.

Another set of rules, namely, a set of clustering rules 428, is provided to the presentation cluster block 414 for determining which information, if any, to cluster or group. The block 414 also receives as input, user intent query 440, from a user, and applies the rules 428 to the latter. The rules 428 are used by the block 414 to group information received from the mapper 412, based on the user intent query 440, and in the process additional apply a set of dynamics (time) rules 430 thereto. The rules 430 serve to identify what is to be looked at to find what has information has been changed over time. In this respect, feedback from the user, through 442, is utilized. Similarly, the rules 428 utilize feedback from the user. Additionally, feedback from the user is utilized, at 434, to accumulate concept-based information and definitions in a Wiki-style fashion.

The presentation cluster block 414 generates output data clusters 416. The cluster 416 information may be displayed and/or presented in other manners, such as with an Application Programming Interface (API), and it further may receive user feedback and use the same to further refine rules for clustering and similarity mappings.

The rules 426, 428, and 430 are independent of one another in some embodiments of the invention. In other embodiments, information flows there between. Advantageously, these rules, partly because they are applied at different stages in the processing of the data 406, allow for a learned and conceptualized process as opposed to a hard decision. For example, in current techniques, where only one set of rules are utilized early on in the processing of the data, a hard decision is made with no flexibility to alter this decision thereby increasing the risk of mis-categorization and/or identification of relevant information. In contrast, thereto, the different sets of rules of the embodiment of FIG. 4, breakdown categories, such as similarity, display, and history, allows configuration of various aspects thereof.

By way of example, in prior art techniques, where the data is regarding electronic devices and a cell phone is to be identified, where the single set of rules, made early on in the process, is based on the lack of a keyboard, and a central processing unit, the device may be erroneously identified as an electronic tablet, with no recourse. Whereas, the embodiment of FIG. 4 allows for progressive learning of various attributes of the device by, for example, using the above exemplary rules as the rules 426 but based on the rules 430 and 428, introducing attributes, such as size of the device, that allow for a more accurate identification of the device. And further, due to the user-feedback and query, allow for dynamically altering the rules.

Use of various rules, such as rules 426, 428, and 430, at various stages of processing, allows flexibility in applying the rules to achieve greater accuracy of clustering. In medical applications in particular, information is oftentimes duplicated for various reasons, such as lack of standardization of names of medications, shorthand identification of information, and a slew of other reasons. In this regard, flexibility of applying rules is vital. While three sets of rules are shown in the figures and discussed herein relative to various embodiments, it is understand that a different number of rules may be employed.

For a better understanding of the flexibility the rules of FIG. 4 offers, an example is now presented. Suppose the data 406 carries medical information for which a particular condition, e.g. diabetes, is to be detected. Rule 426 allows for a similarity between lab results and "diabetes" to be identified but that is nearly where the application of rule 426 ends until further information is known and extracted later in the processing of the data 406. Namely, when rule 428 is applied to the outcome identified by Rule 426, the lab results are crawled or inspected for "diabetes" or another identifier for "diabetes". Additionally, the presence of various relevant labs is detected and the association between the presence of the labs and the problem of diabetes and perhaps, hemoglobin A1c (a measure of average blood glucose concentration over the past 30 to 120 days, used in the diagnosis and treatment of diabetes) is made. Next, the rule 430 is applied to the outcome of the application of rule 428 where patient data is used or a correlation between a problem and a treatment for a large percent of the patient population is made. Specifically, the percentage of patients with diabetes is detected. The parameter of time allows for the latter detection, otherwise, for example, at the application of rule 426 or even rule 428, a large patient base could not have been correlated.

The user input and the user feedback at 418 all help in the clustering of data. At the application of rule 426, a determination is made as to how things are similar until a user asks about the similarity after which a more educated application of rules is performed. Thus, no decision is made until the end or at the output of the block 414, in real-time.

During the application of rule 426, the system is informed of key parameters but not how to put the data together. Then, during the application of the rule 428, the system is informed of how to put the data together (cluster) by aligning the data in a particular manner. Application of rule 430 determines how things change over time, or not, but not what the correlation or similarity actually is, which is generally done through the rule 428. Part of the reason for splitting the rules is to delay decision-making as long as possible in an effort to cleverly use more information, such as that provided by the user, for an increasingly accurate finding.

The outcome of the data cluster 416 is a plurality of work items which may be transmitted to another processor, system, user, or any other entity.

As with the blocks of the health information management system 112 of FIG. 1, it is understood that the blocks shown in FIG. 4, such as block 410 and 414, and 416 may be independently a machine and/or processor or a part of a machine and/or processor. They may alternatively, be carried out in software programs.

Figure 5A:
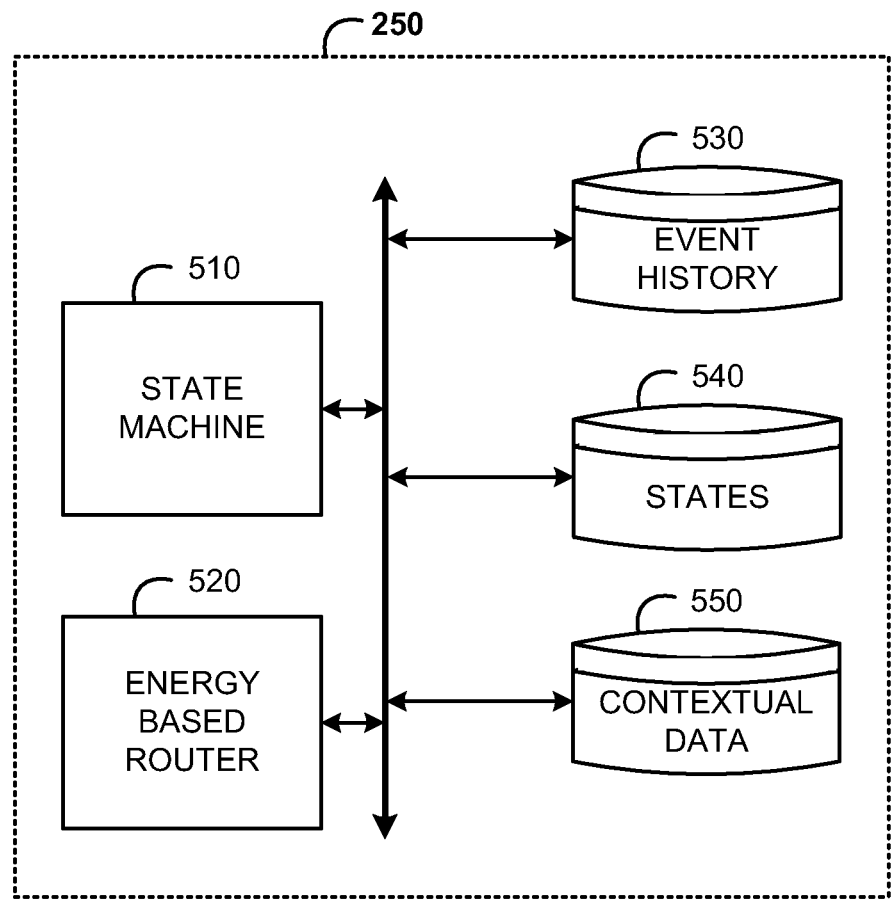
FIG. 5A shows an example embodiment of the workflow manager which includes state machines for workflow configuration and an energy based router, in accordance with an embodiment.

Returning to FIG. 2, after the bundler 240 performs the contextual clustering of the data elements in order to generate work items, the next component of the health information management system 112 is a workflow manager 250 that generates workflows and ensures efficient routing of the work items through the workflows. FIG. 5A provides a more detailed illustration of an example embodiment of the workflow manager 250.

Fundamentally, the workflow manager 250 is composed of two key elements: one or more state machines 510 capable of configuring the workflows, and an energy based router 520 for the efficient routing of the work items through the configured workflows. When configuring the workflows, the state machine 510 leverages the possible states 540, the current action, event history 530 for the work item, and contextual data 550 regarding the user of the system in order to configure the workflows in a manner that is responsive to the needs of the user. The workflow configurations may be updated after each action for a given work item, ensuring that the workflow is adaptive to a given goal. Examples of workflows are provided in greater detail below.

The energy based router 520 utilizes a scalar reward function in order to optimize the routing of the work items through the workflows in order to most efficiently meet an objective for the user. For example, the objective may be to process the entire data set, maximize reimbursement of MediCare claims, or identify disease codes that meet submission requirements, in various embodiments.

Figure 5B:
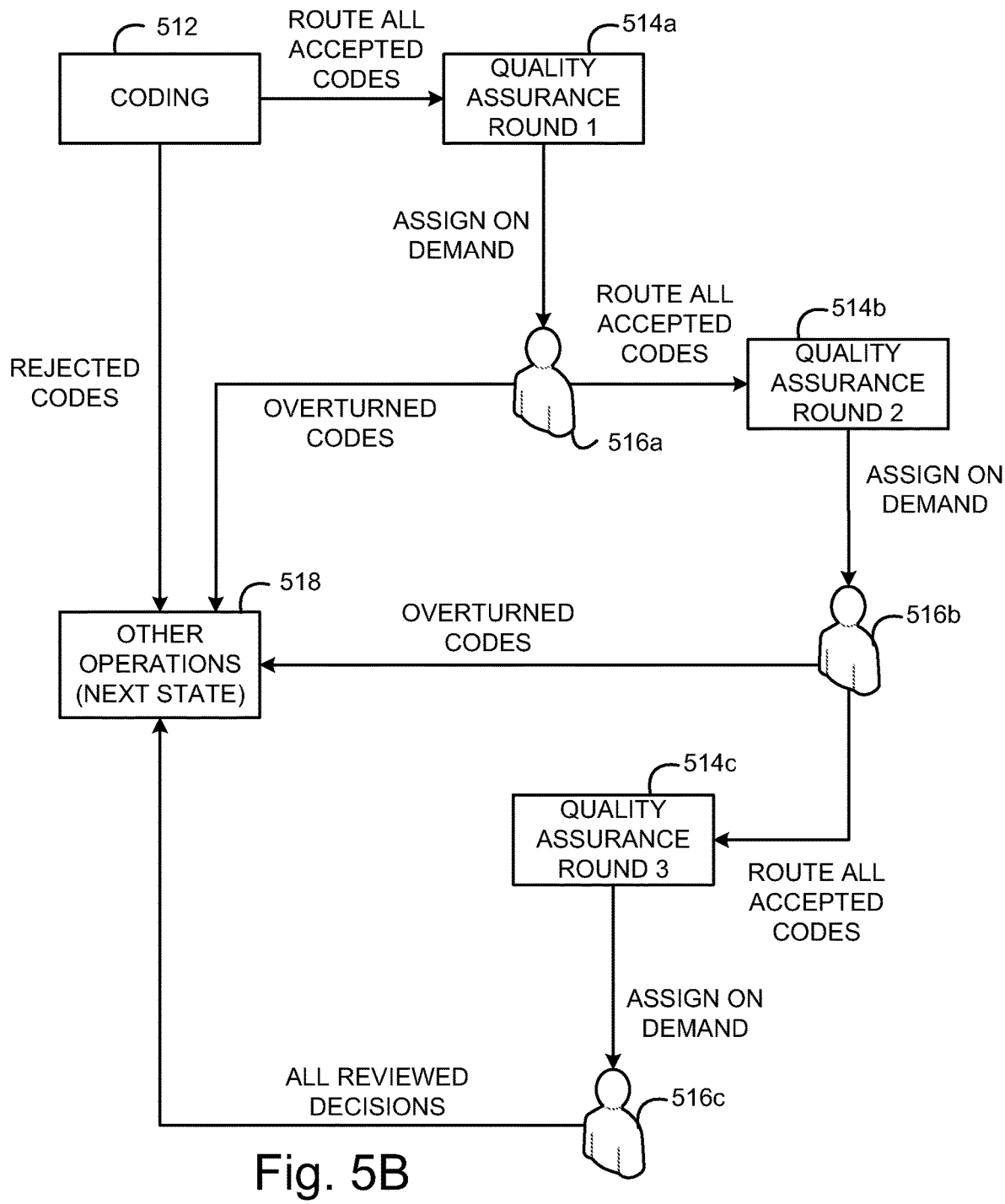
FIG. 5B shows one example of a state machine configuring a workflow, in accordance with an embodiment.

Returning to FIG. 2, after the workflow has been properly configured and routing determined, the work items may actually be iteratively processed through the workflows 260. FIG. 5B provides one such example diagram of a configured workflow for coded record review for quality assurance. Note that this is but one example of a workflow, and not exhaustive of even the workflows possible for code quality assurance processes. Rather, this example is being provided for clarification and to help illustrate what is being referred to by the term 'workflow'. In this example workflow, a set of coded records 512 are generated. Rejected code work items are immediately sent to other operations 518, which is effectively the finishing point for this example workflow. However, all accepted codes may be routed to a quality assurance round 514a, which on demand, may route the record set and coding to a human coder 516a for review. The human coder 516a may access the records that evidence the code via an online portal or other suitable interface. Upon reviewing the records, the coder 516a may accept the code, or reject (overturn) the code. If the code is overturned, the work item may be routed to the other operations 518. All accepted codes however are forwarded to a secondary quality assurance round 514b, that processes the codes in the same manner as the earlier round. Accepted codes are then sent to a third and final quality assurance round 514c, where all decisions made by the third coder 516c are provided to the other operations 518.

While in this example diagram three distinct quality assurance levels are illustrated, in alternate embodiments records may be subjected to fewer or more review cycles based upon system configuration. Moreover, in even more sophisticated workflows, the codes may be routed to coders based upon subject matter, and number of coder reviews may be variable based upon a calculated confidence index for the evidence supporting the code.

Figure 6:
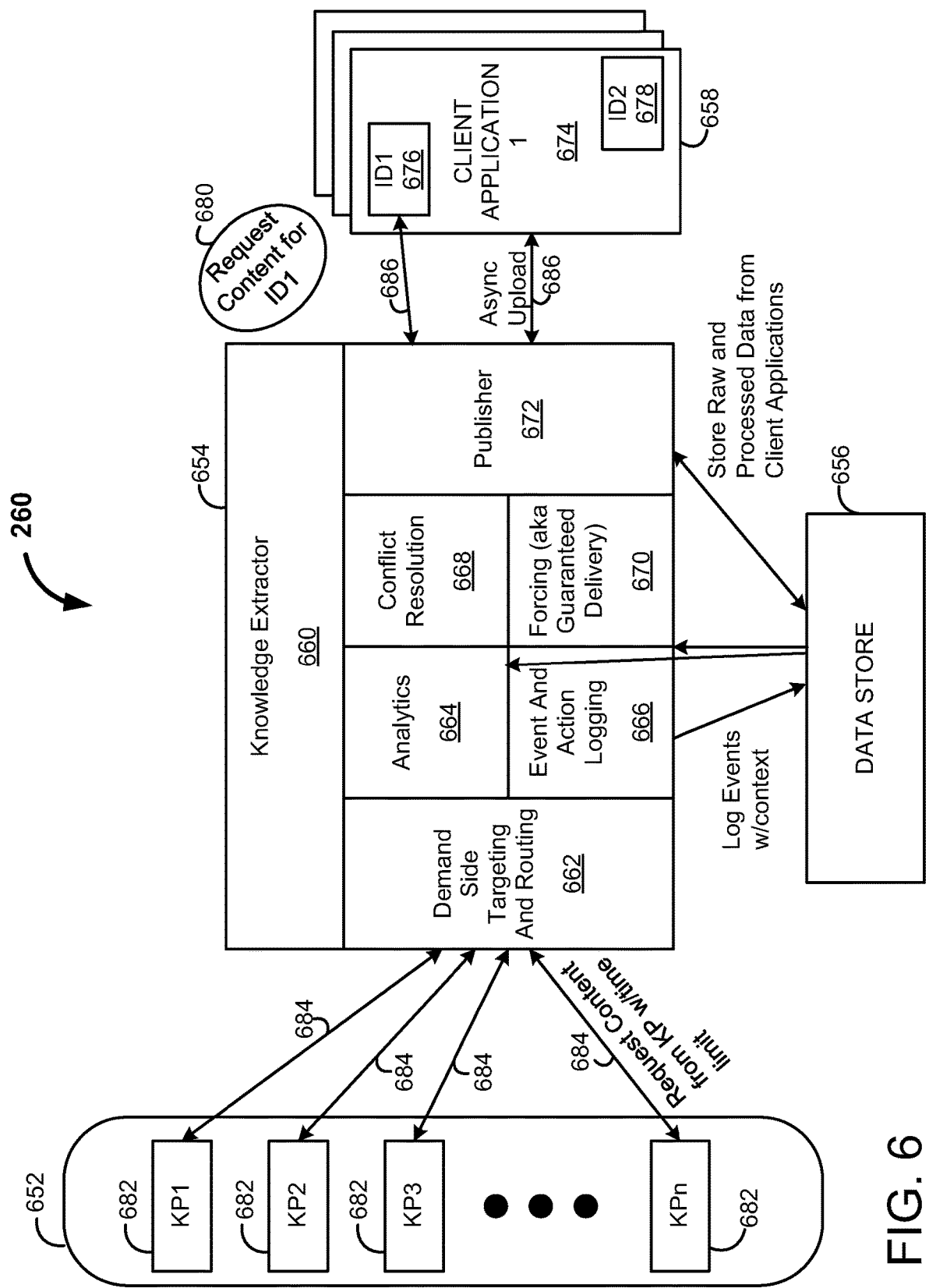
FIG. 6 shows an example diagram of a knowledge extractor within the event stream workflows, in accordance with an embodiment.

Moving on, FIG. 6 provides detail of one embodiment of where knowledge extraction is performed on the work items. Knowledge extraction may be employed by agents in order to generate additional inferred events.

In these knowledge extraction embodiments, the workflow may be best characterized as a series of agents that perform some action on the work items. An "agent", as used in the context of this application, is any process that consumes an event stream/work item, along with other external sources of knowledge (such as dictionaries, machine learning models, etc.) and creates new inferred events that are added to the original event stream. Agents may act iteratively on an work item, where one agent consumes the work item and adds inferred events to it form a secondary event stream/work item. Then a second agent may consume the secondary work item and infer yet other events to form a tertiary event stream/work item. Then the first agent may consume the tertiary event stream to form yet another version of the work item.

Agents utilize knowledge extraction, and/or first order logic (a.k.a. first order predicate calculus) queries over the work item in order to generate the inferred events. Greater detail is provided below regarding the knowledge extraction and querying abilities of the agents.

Eventually, a final work item may be generated where the agents have no further events to add to it. This final work item may be then made available to subsequent applications for downstream analytics, such as quality measures, care optimization, etc.

The system 260 is shown to include a knowledge provider block 652, a knowledge extraction and exchange unit 654, a data store block 656, and a client application block 658. The block 658 executes client or user applications 674 using event streams generated by the knowledge extractor 660 (in addition to event streams generated by querying agents).

The block 652 is analogous to the sources 114 of FIG. 1 and is shown to include a number of knowledge providers 682, with each knowledge provider being analogous to one of the sources discussed above relative to the sources 114. The knowledge extraction and exchange unit 654 may include a back-end medical processor. The knowledge extraction and exchange unit 654 is shown to include a demand-side targeting and routing block 662, an analytics block 664, an event and action logging block 666, a conflict resolution block 668, a forcing (or guaranteed delivery) block 670, a publisher block 672, and a knowledge extraction block 660. The block 658 is shown to include one or more impression domain (ID) blocks 676 and 678. While two ID blocks are shown in FIG. 6, it is understood that any number of ID blocks (e.g. problems, procedures, medications, allergies, "did you know?", patient safety items, billing enhancement items, and the like), as required by a user of the system 260, may be employed.

The knowledge extraction and exchange block 654 generally manages the overall process of delivering "content" to the ID blocks 676 and 678 in the form of event streams/work items, including managing the data store block 656, managing interactions with the knowledge providers 682 and determining which results to present to the client application block 658 when a request of "content" is made by one of the ID blocks 676 and 678 and how to rank the requested results. An example of a request is shown at 680 in FIG. 6 where the block 676 is making the request. "Content", as used herein, refers to any information pertinent to the ID embodied as an event or event stream, for example a query string, image or hyperlink.

The data store block 656 is generally a storage device or a database storing raw and processed data received from the block 674, through the unit 654. Raw data is data that comes directly from the application 674. Processed data is data that has been processed or optimized for efficient use by knowledge providers. The knowledge extraction and exchange block 654 causes actions to be logged with context into the data store block 656 when data is being stored therein.

The knowledge extraction and exchange block 654 communicates with the client application block 658 bi-directionally and typically asynchronously such that when there is a change to the underlying data in the application of the block 658, such as an update to the patient chart, the block 658 sends this updated data to the publisher block 672. The client application block 658 is a client or user application with each of its ID blocks querying for and displaying its particular impression domain content. By way of example only, impression domain content includes items such as problems, procedures, medications, allergies, "did you know?", patient safety items, billing enhancement items, and so on. Each ID presents information to the user that is relevant to the specific patient/user/context at the time the information is displayed. For example, a patient safety ID would present a patient's past history of myocardial infarction to a primary care provider if that event were not noted as structured data the user's EHR application. The publisher block 672 receives content requests from the ID blocks 676 and 678 and in response returns content to be displayed in the blocks 676 and 678. Further, the block 672 receives actions (such as clicks) from the ID blocks 676 and 678, receives raw data (such as patient chart updates) from the application block 674, and manages storage of data in the data store block 656 (including action logs, raw client application data event streams, and data extracted for the specific needs of the knowledge providers 682 of the block 652).

The demand side targeting and routing block 662 routes content requests to the different knowledge providers 682, received from the client application block 658 by selecting a subset of knowledge providers in real time which it considers most relevant to the current patient/user/context based on criteria provided by the knowledge provider, such as "patient covered by Medicare Advantage", "user is a cardiologist", or "query includes the term EKG", and subsequently receives their responses, through the knowledge provider links 684. In some embodiments, if a knowledge provider 682 with an outstanding content request does not respond within a prescribed amount of time, the request is cancelled.

The conflict resolution block 668 receives content from the demand side targeting and routing block 662 and advantageously determines which of the responses from the knowledge providers 682 to pass to the forcing block 670 and in which rank order. The conflict resolution block 668 uses the content from the ID block 676 or 678 (e.g. patient, user, query) along with analytics on the performance of past knowledge provider results to determine which results are most likely to be useful. For example, if an endocrinologist user always clicks on the hemoglobin a1c history after performing a diabetes search, the ID for labs may start automatically displaying the history in response to a diabetes context for that particular user. If enough endocrinologists perform the same action, the ID for labs may start automatically displaying the history for all endocrinologists, whereas such an automatic action might not be performed for general practice users searching for the same diabetic context.

The forcing block 670 receives ranked and selected results from the conflict resolution block 668 and further determine to potentially override the ranking determined by the conflict resolution block 668. For example, if only one result can be displayed in a particular ID block, and it receives a high-value reimbursement result and an important patient safety result, the patient safety result might be given priority over the reimbursement result.

The event and action logging block 666 stores action data, such as click-through actions in the data store block 656, along with context information (ID context, date, time). Action data refers to end user actions e.g. clicking on a particular content that is displayed for more information or history.

The analytics block 664 computes summary statistics for events and actions and places them in the data store block 656 for use by the conflict block 668. End user statistics like click-through rates and dwell times may also be computed by the analytics block 664.

Each of the ID blocks 676 and 678 sends a request to the knowledge extraction and exchange unit 654 asking for certain kinds of result (text, images, links, diagnosis codes) from the knowledge extraction and exchange unit 654. A typical request includes the number of results desired and the context of the request, such as patient identifier, user identifier (and user role, such as specialty, physician or coder or medical assistant, etc.) and the search query. The ID block 676 or 678 is responsible for determining how the results are presented to the user of the system 650. For example, when an action is taken, such as a click on a search link, the ID block 676 or 678 also submits this information to the action logging block 666.

Each of the knowledge providers 682 computes and returns results that are relevant to a particular ID block request. In some embodiments, the knowledge providers 682 have access to the data store block 656. For example, a knowledge provider might return PubMed articles, up-to-date articles, or best treatment practices that are relevant to the patient/user/context.

Figure 7:
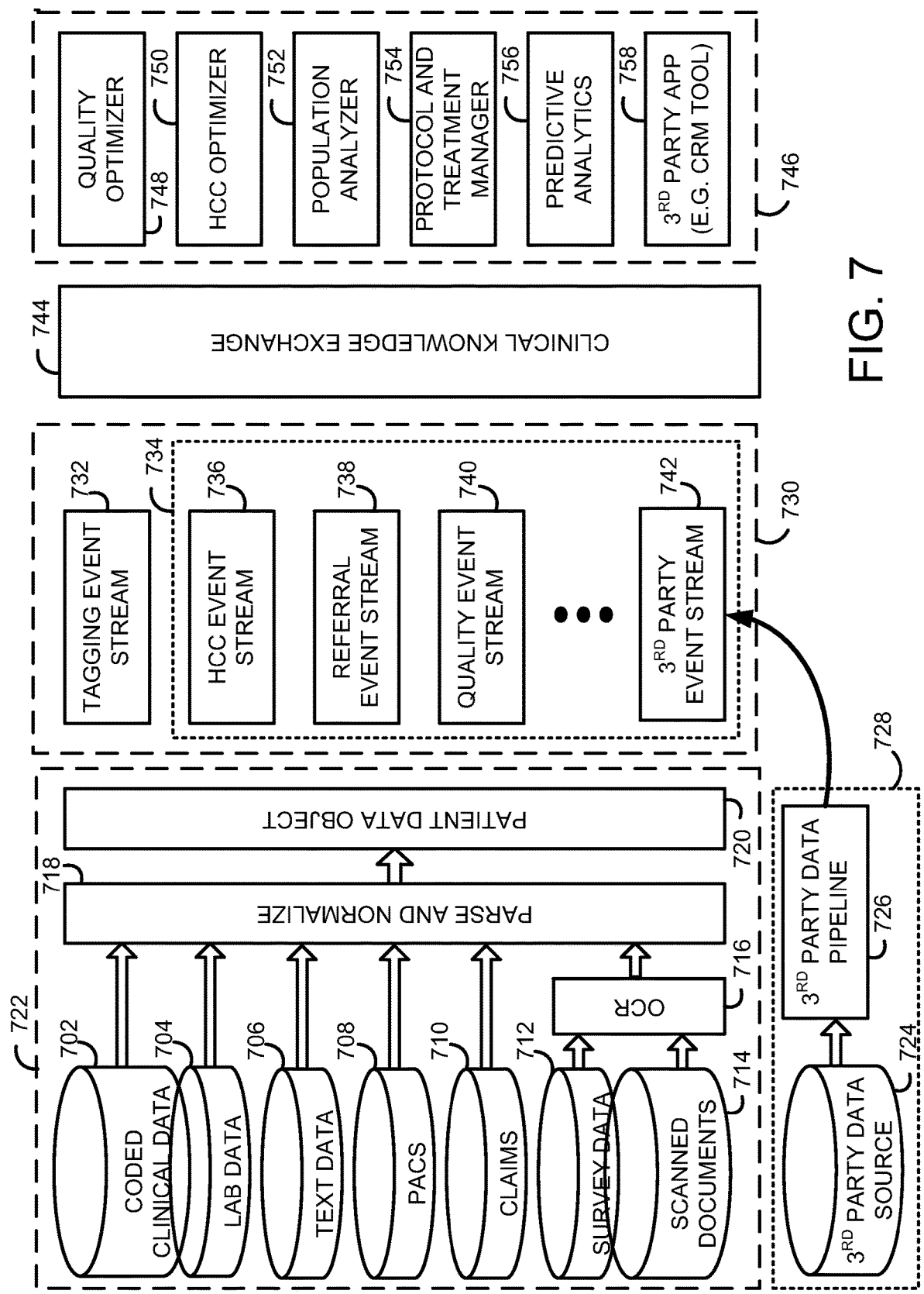
FIG. 7 shows an example diagram of an event stream workflow, in accordance with an embodiment.

Referring to FIG. 7, a data flow diagram is provided which illustrates how raw medical information is handled, managed and manipulated in a manner to enable consumption by applications.

In this figure, a comprehensive set of data sources are displayed. These include coded clinical data 702, lab data 704, textual data 706, PACS 708, claims 710, survey data 712 and scanned documents 714. All these data sources are available internally within an healthcare organization. These data sources may be the same or similar to those illustrated at FIG. 1 at part number 114, and part 652 of FIG. 6.

The survey data 712 and scanned documents 714 are not in machine readable form and must be converted by optical character recognition (OCR) to a format that may be utilized by the computer system. All the raw data (including OCR data where appropriate) are parsed and normalized by a module 718. This normalized data is then indexed, by an indexing module, to generate a patient data object 720. The patient data object 720 may be stored in a data store, such as that shown at part 656 of FIG. 6. The entire data flow from raw data sources, to OCR as applicable, parsing and normalization, and indexing into a patient data object is referred to as a data aggregation pipeline 722.

In addition to the internal data aggregation pipeline 722, a third party data source 724 may be similarly prepared via a third party data pipeline 726, within the confines of the third party system 728.

The resulting patient data object 720, and third party data object from the third party data pipeline 726 may be provided to a big data index pathway 730 which is a function of the knowledge extractor 660 of FIG. 6. The patient data object 720 may undergo meta tagging by the tagging module at 732. From the tagging and initial work item is generated.

Note that, "events", as used in this application, are defined as facts (something that is true or false) that has occurred in a specific time for a specific subject (in the clinical context, it could be the patient, an organization, etc.), attributed to a specific agent (i.e. a cause—could be a provider, organizations, etc., or a some combination of them), a source (original source of where that fact originated from), and an episode grouping (typically an encounter in the clinical context). An event can also be associated with a collection of named values. An "event stream" is a collection, or set, of events that have been contextually bundled together.

In order to provide more clarity into the form of an event, an example is provided below. In this example a patient, John Sample, has undergone a medical examination on Nov. 26, 2011 which generates a medical record. A portion of this example medical record, including the physician impression and notes, is provided:

IMPRESSION: The patient is a 68-year-old gentleman admitted for:
1. Pneumonia, chest x-ray confirms the same with shortness of breath.
2. Ischemic cardiomyopathy with abnormal stress test, inferior defect, ejection fraction 30% with elevated BNP, possibly secondary to underlying infection versus decompensated congestive heart failure.

The medical system is capable of parsing, normalizing, indexing and tagging this medical information into an event with the following structure:

<Patient John Sample, "depressed contractility", GPRO2012:HF_LVSD_CODE, 11/26/2011, 11/26, 2011, Outpatient Encounter on 11/26/2011, Document Titled "Ea-Cardiology Consolut" dated 11/27/2011 authored by chris cardiologist, Inferred Event from Document, "EF:30%", <snippet goes here>, ClinicalEvent, 11/26/2011, End-of-Time>

In this event, a number of values are recorded, these include:
1) The Subject, which is a required element of the event. In this example, the subject is "Patient John Sample".
2) The Evidence Used to Infer the Event. In this example the evidence is the term "depressed contractility" in the physician's impressions; however the evidence may include any of a collection of terms, output of a machine learning model, etc.
3) The Fact that was inferred from the evidence. This too is a required element of the event. Here a code is the Fact being inferred.
4) A Start Date of the event is also required. In this case, the start date is the date of the medical examination.
5) Likewise, an End Date of the event is required. In this case, the end date is the date of the medical examination.
6) An episode level Grouping may also be provided in the event as an element. Some analytical tasks require an episode level grouping. In this example, the grouping is an "outpatient encounter" on the specified date. Other episode groupings could include 7) The source of the event is also required for review and auditing purposes, and thus is typically included as an element of the event. Here the source is the example physician generated document. Sources can include any of those illustrated above in relation to FIG. 7.
8) The type of event is also required for audit, review and feedback loop based improvement of algorithms. In this example, the type of event is an inference from a document.
9) Named values may also be a component of the event. In this example the named value is "ejection fraction 30%"
10) A Snippet of the source may also be provided in the event. The snippet may be important for review and feedback loop based improvements. In this example "snippet goes here" was utilized for the sake of clarity. However, in an event such as this the snippet may include text such as: "Nuclear myocardial perfusion scan with adenosine in the office shows depressed contractility with inferior reversible defect. Ejection fraction is 30%."
11) The event classification is the next element of the event. Here the event classification is "ClinicalEvent". Other event classifications could include Administrative events, Eligibility events, Billing events, Audit Events and others.
12) Lastly, Expiry Information is provided as a date range (validAfter, validBefore). The Expiry Information indicates what time periods the event is good for. In this example the event starts as of the clinical diagnosis date, and extends into the future indefinitely. Other events may have expiration dates.

A set of events is an event stream. Once tagged at 732, the work item is provided to one or more agents 734 for inference of other events and the generation of expanded event streams. An "agent", as used in the context of this application, is any process that consumes a work item, along with other external sources of knowledge (such as dictionaries, machine learning models, etc.) and creates new inferred events that are added to the original work item. Agents perform these inferences using knowledge extraction, as disclosed in detail previously, and first order logical queries.

For example, an HCC agent could consume the initial work item and generate an HCC event stream 736. This HCC event stream could be consumed by a referral agent to develop a referral event stream 738. The referral event stream 738 would include all the events of the HCC event stream 736 in addition to the newly inferred events generated by the referral agent. Other agents may include a quality agent, third party agents, and the like, each capable of generating a corresponding quality and third party event stream 740 and 742, respectively.

In some embodiments, each agent may iteratively process the work items; thus the quality agent may process the initial event stream to generate a quality event stream which may be then processed by the third party agent to generate a third party event stream. The quality agent may then consume the third party event stream (iterative functionality) to generate a new quality event stream that is further expanded by new inferences based upon events generated by the third party agent. Clearly, as the number of agents increases the number of iterations increases exponentially. This results in very rich event streams.

Eventually, despite repeated iteration, no new inferences are able to be generated. This final event stream is then provided to the clinical knowledge exchange 744 for distribution to downstream applications. The clinical knowledge exchange 744 enables the consumption of work items by applications 746. Some applications considered by this application include a quality optimizer 748, an HCC optimizer 750, a population analyzer 752, a protocol and treatment manager 754, predictive analytics 756, and other third party applications 758. In some embodiments, the downstream applications may be a combination of internal applications and external third party applications. In some embodiments, applications may be patient independent, patient specific and population specific.

Further, the generation of event streams and the clinical knowledge exchange allows for third parties to configure customized workflows, map the output format of work items via the third party applications, and publish and index work items in a consolidated platform. The applications that these third parties develop are then able to consume their configured event streams. The platform, via the clinical knowledge exchange, may provide authentication and access controls for the applications in order for them to work with multiple work items.

II. Methods of Workflow Management

Now that the systems for the health management system have been disclosed in detail, attention will be directed toward the processes of workflow management within a medical information system. These processes are provided in conjunction with exemplary flowcharts. These flowcharts are merely examples of specific embodiments of some processes employed to perform the annotation, coder marketplace management, and data warehouse presentation.

As such, the following flowcharts, and associated text, are intended to be merely illustrations of embodiments, and not limiting the scope of the present invention to any specific embodiment.

Figure 8:
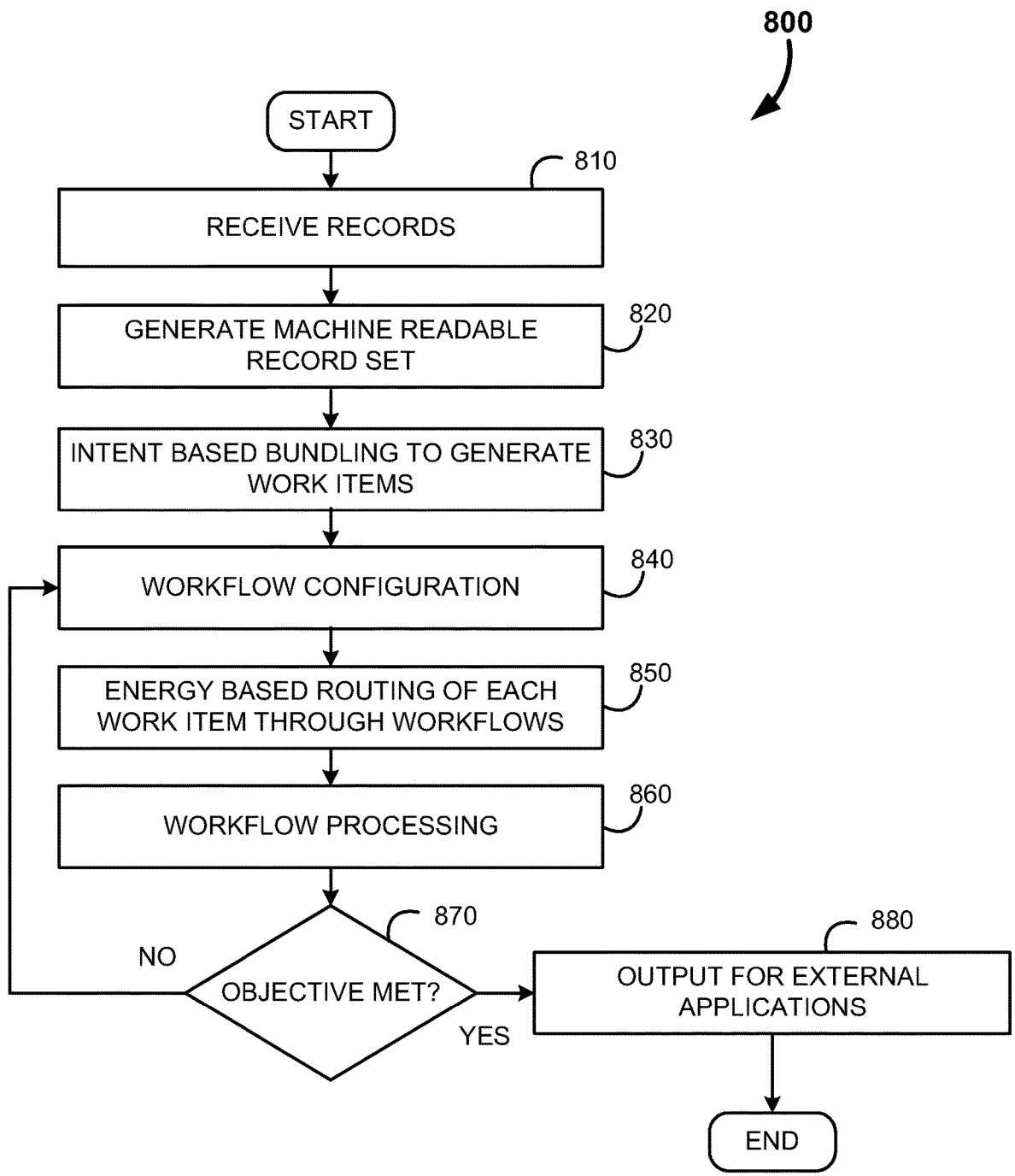
FIG. 8 shows an example flow chart for the process of workflow management and processing, in accordance with an embodiment.

FIG. 8 provides a high level overview of one example processes for medical records management utilizing bundling, workflow configuration and efficient workflow routing, provided generally at 800. In this example process, the records are first received (at 810). After documents are received they may be processed in order to generate a set of machine readable objects (at 820). Processing of the records into machine readable data has already been touched upon; however, FIG. 9 expands upon one embodiment of this processing operation.

Figure 9:
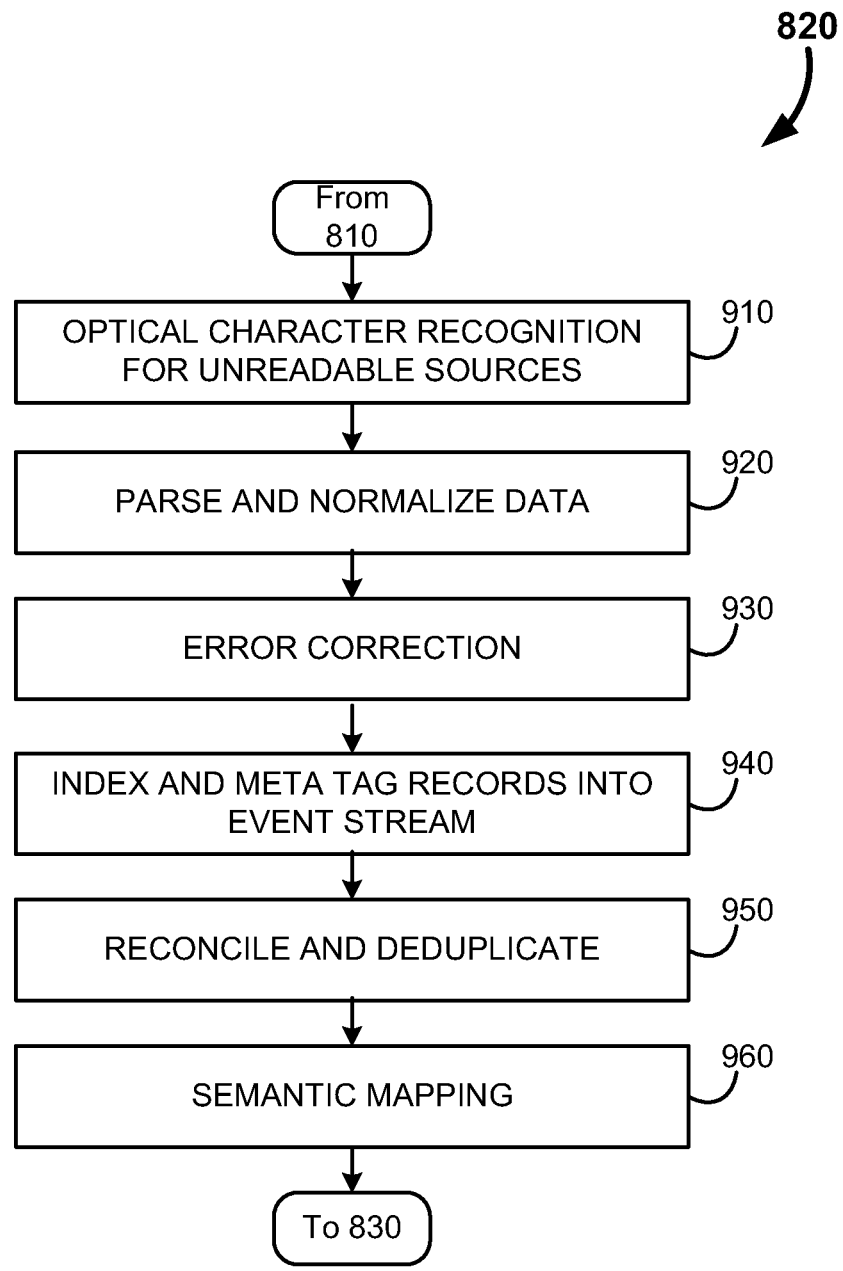
FIG. 9 shows an example flow chart for the process of generating a machine readable dataset, in accordance with an embodiment.

Turning to FIG. 9, initially unreadable records may be subject to optical character recognition (OCR) for the generation of a text stream (at 910). All the raw data (including OCR data where appropriate) are parsed and normalized (at 920). Normalized data is then subjected to an error correction step (at 930) which removes duplicate records, incomplete records, and nonsensical records.

The corrected records may then be provided for indexing and meta tagging (at 940). Indexing takes processed documents and converts them into formats that make it easy to quickly search across a large collection of documents. Semantic meta-tagging embeds information into the medical information that is relevant thereto and that can be later used to search for certain information for the purpose of reconciliation (at 950) and search, among many others. Next, the records undergo semantic mapping (at 960). Semantic mapping may leverage natural language processing in order to extract conceptual data from the records.

Returning to FIG. 8, after the machine readable set has been generated, intent based bundling is performed to generate work items (at 830). The process for bundling the machine readable data elements is described in greater detail in relation to FIG. 10.

Figure 10:
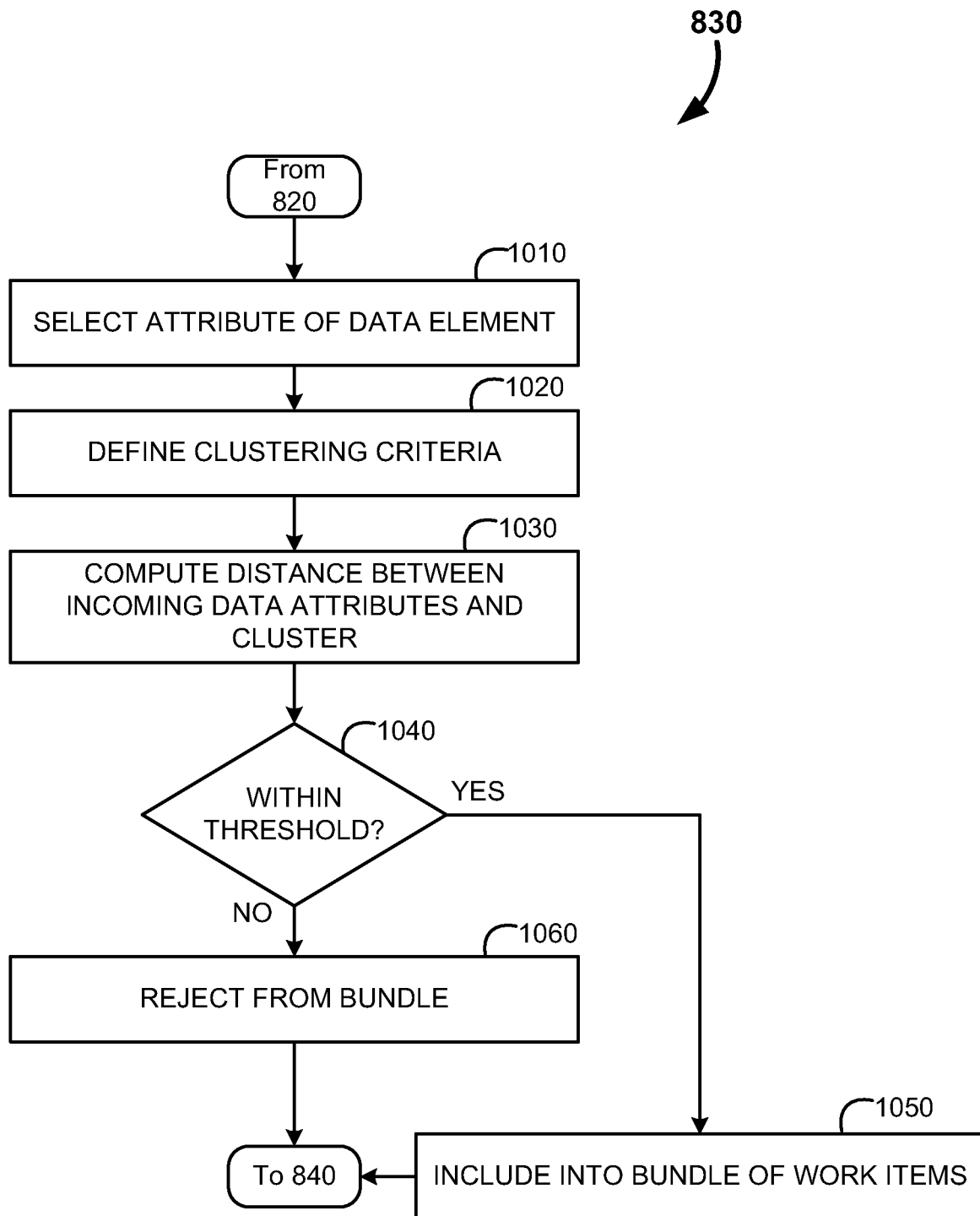
FIG. 10 shows an example flow chart for the process of contextual bundling, in accordance with an embodiment.

In FIG. 10, an automatic or manual, or a combination, of attribute selection is performed (at 1010) by applying rules 426 and 428, in accordance with a method and embodiment of the invention. Accordingly, attributes to be included in clustering are selected. For example, for a presentation of medications, several attributes might be included. To present results to a user, another machine, processor or the like, for a medication history intent, medication brand name, generic name, coding system, drug code, and ingredient might be selected. This may be done by a user, manually, or automatically by the block 414, in an exemplary embodiment of the invention.

Next, the criteria for clustering relevant combinations is defined (at 1020), manually, automatically or using a combination thereof. The matching criteria for each of these attributes are defined as a maximum distance along with an appropriate definition of distance. Examples of "maximum match distance" are "exact match", "close match", "loose match" or distance <x where x is an appropriate maximum distance. Examples of distance measures are numerical difference, any edit distance, semantic distance, abstract distance along an ontology or graph, etc. Rules for relevant combinations of the selected attributes are also defined during this step. In some methods and embodiments, attributes can be combined to create a composite threshold that the data 406 can be measured against. With reference to the medication history intent presented hereinabove, all medications in the patient history that are close matches on brand name or generic name might be included, along with exact semantic matches on a particular drug ingredient or exact numerical matches on a group of related drug codes.

Next, the distance between the data 406's attributes and cluster is computed (at 1030). For example, it is determined (at 1040) whether all distances are less than the maximum distance threshold and if so, the cluster is updated to include such data in the work item bundle (at 1050), otherwise (at 1060) such data is rejected (not included) from the work item.

Figure 11:
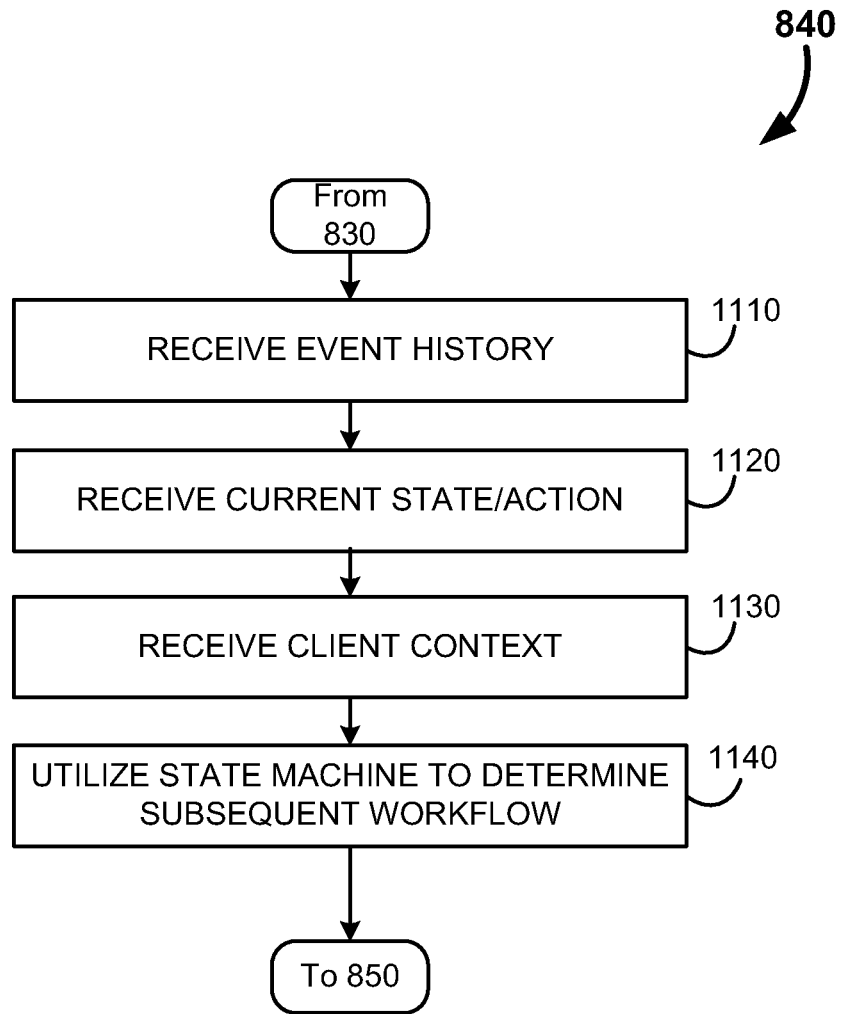
FIG. 11 shows an example flow chart for the process of contextual workflow configuration, in accordance with an embodiment.

Returning to FIG. 8, after the work items have been generated via bundling, the next process is to contextually configure the workflows (at 840). FIG. 11 provides a more detailed view of the process for workflow configuration. In order to configure the workflows, a variety of inputs need to be collected. These include the event history for the workflow (at 1110), current action (at 1120), and user context (at 1130). These inputs are fed into a state machine in order to determine the next action in the workflow sequence (at 1140).

The advantage of such a system is that by taking into account the user's intent, and the previous actions taken in the workflow, the workflow may be configured dynamically and be reflective of the needs of the client user. Additionally, the workflow configuration may be an iterative process, as actions are taken the workflow may be updated in relation to the results of the previous actions.

Figure 12:
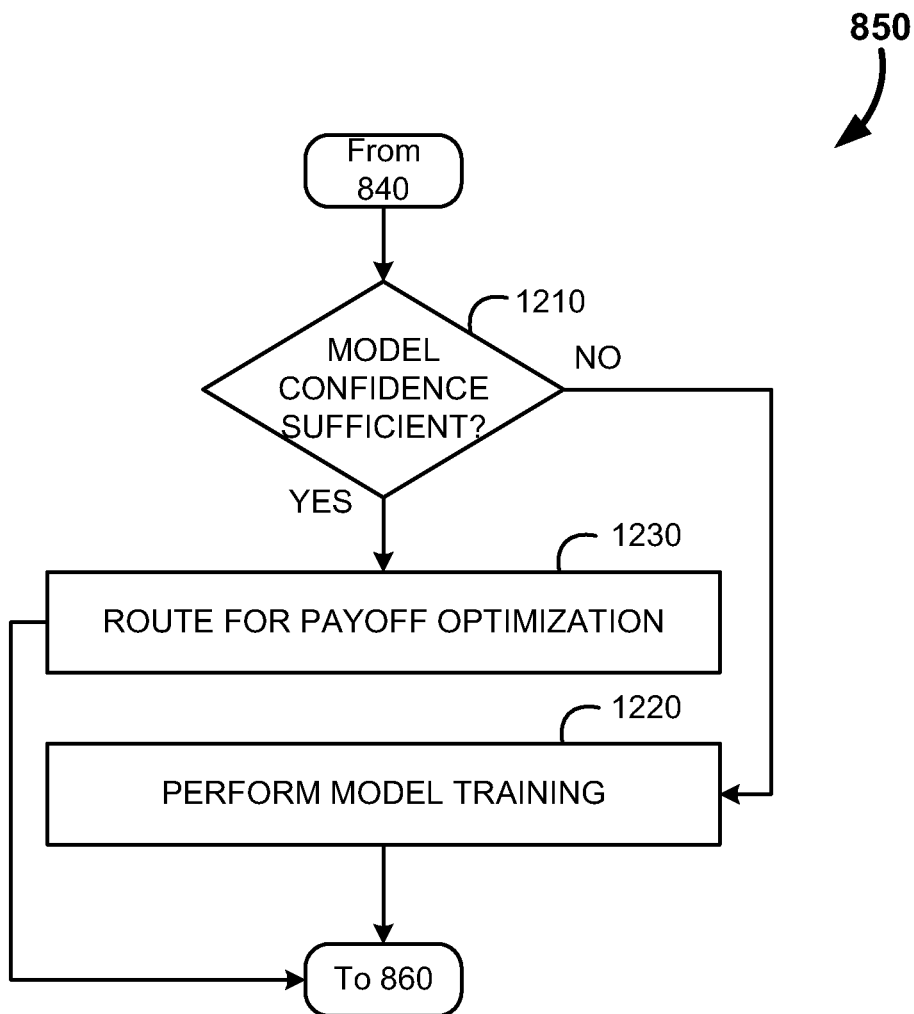
FIGS. 12-14 show example flow charts for the process of energy based routing, in accordance with an embodiment.

Returning to FIG. 8, after workflows have been configured, the next process is to perform energy based routing for each of the work items through the configured workflows (at 850). FIG. 12 provides a detailed view of this energy based routing process. Initially a determination is made whether a model utilized by the system is sufficiently robust in order to be sufficiently accurate (at 1210). The model utilized by the system is used to determine what the probability of an outcome will be for a particular work item being processed by a given action within the workflow. When the workflow being employed is for hierarchal condition categories (HCC) reimbursement by MediCare, for example, the model may indicate the probability of a given code with the given evidence found in the workflow will be accepted by MediCare for reimbursement, and the amount typically reimbursed for. Thus, utilizing such a model, work items that are most likely to achieve a given objective (in this example maximizing MediCare reimbursements) may be prioritized for routing through the workflow over lower payout work items.

Determination of model confidence may be achieved utilizing a number of statistical techniques that are known in the art. Sample size for models generation, time since model was generated, and accuracy of model predictions may all be utilized in order to determine if the model is sufficiently accurate. In some embodiments, even for models that appear to be accurately predicting results of work items being processed by the various workflows, it may be desirable to update the model after a given time has elapsed due to the dynamic nature of datasets, trends in HCC acceptance, or other variables.

Depending upon the confidence of the model, the method may either enter an exploration mode for the refinement of the systems model intelligence (at 1220), or may route the work items in a manner to optimize for a given objective (at 1230). The objective being optimized for is dependent upon the system's user. For example, a provider may be interested in HCC reimbursement optimization, whereas a physician may be interested in collecting all evidence for a particular pathology in a cohort.

Figure 13:
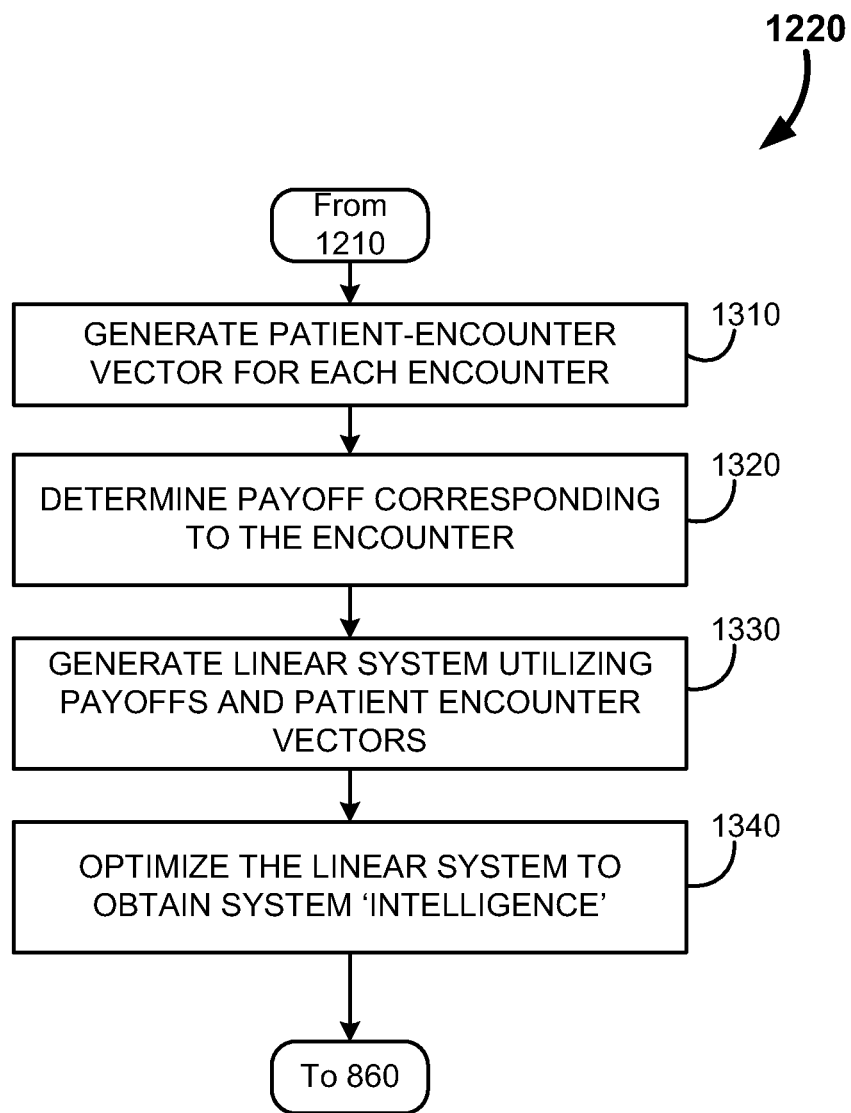
Figure 14:
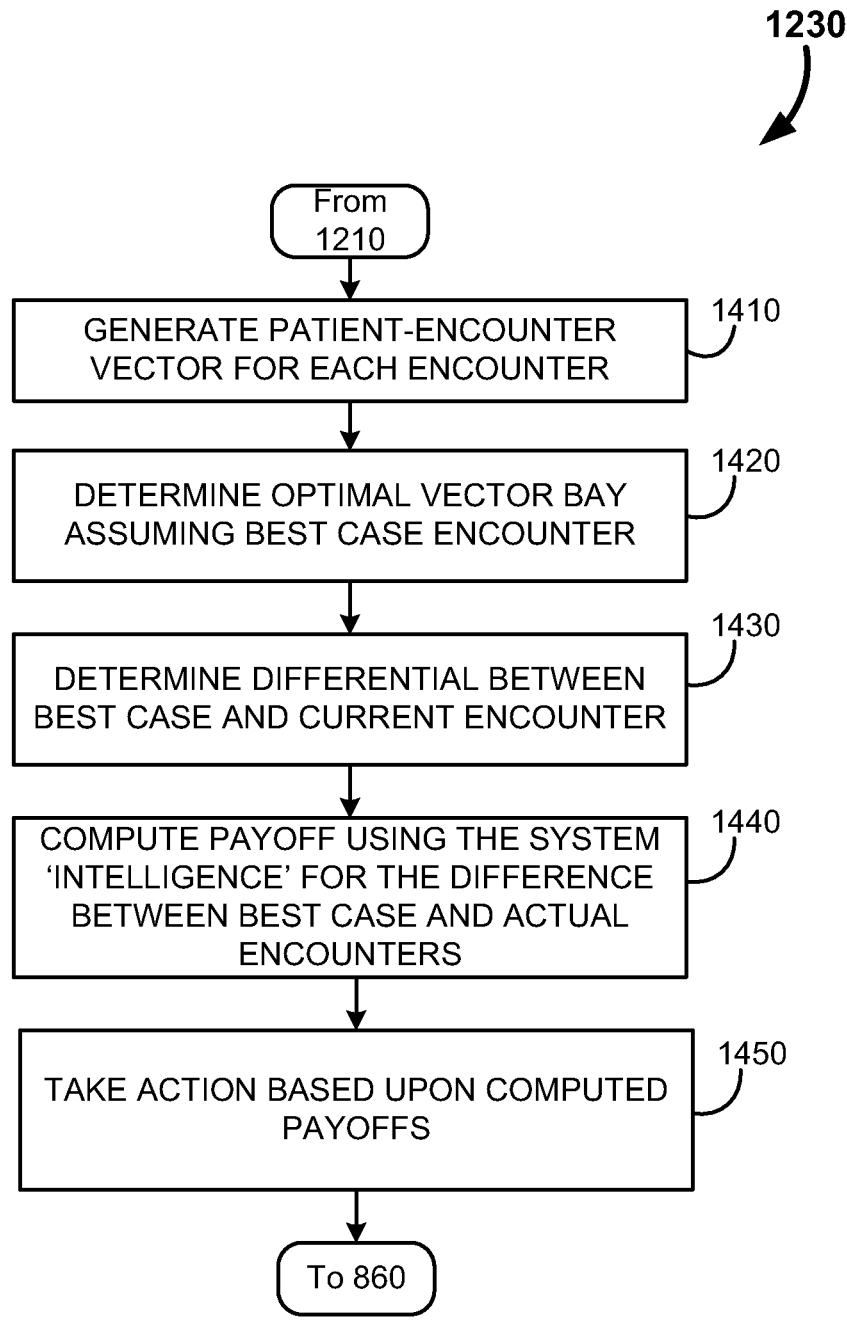

FIGS. 13 and 14 provide more detailed flow diagrams for exploration routing, or routing to maximize the objective, respectively. At FIG. 12 the exploration process is provided. In this process, an intelligence (I) of the system is generated. This intelligence matrix is the model for the outcome of a work item being processed by a particular action. In this example process, claims, encounters, clinical documents, and user context (collectively included in work items), are all utilized by the processor to construct a patient-encounter vector (at 1310). This vector and adjudicated data are used to obtain the payoff corresponding to the encounter (at 1320). All patient encounter vectors and all payoffs are collected to make a linear system (at 1330), which may be optimized to obtain the intelligence model of the system (at 1340).

Likewise, FIG. 14 uses the intelligence model generated in the manner of FIG. 13, in conjunction with encounter vectors to optimize encounters (the energy based exploitation stage). In this example process, the work items include various sources, such as claims, encounters, clinical documents, and user context.

In one example, the steps of FIG. 14 are for application of hierarchal condition categories (HCC) and advantageously identify the first order HCC gap alerts. The patient-encounter vectors are computed, or recalled if previously calculated (at 1410), and an optimal vector is likewise computed under a "best case encounter" according to the organizations objectives (at 1420).

The difference between the best case vector and the actual encounter vector is then computed (at 1430). The corresponding payoffs for these differences are then computed (at 1440) using the intelligences previously calculated. This payoff information is value lost to the organization due to non-optimization of encounters. As such, prompts may be presented to the user, or direct action may be taken, in the order of the payoffs in order to rectify the lost opportunity (at 1450).

Of course, other downstream applications are considered within the scope of this disclosure. For example, beyond hierarchal condition category optimization workflows, other workflows may be employed to optimize quality of care, analyze populations, manage protocols and treatments, and perform predictive analytics, manage customer relationships, and other such downstream applications. It should be noted that this listing is not exhaustive, and any applicable downstream workflow may be employed as desired for system operation and utility.

Returning to FIG. 8, after work item routing through the workflow has been computed, the workflow may actually be processed (at 860). At any point within the workflow processing it may be desired to sample the work items and workflow results in order to ensure quality of the workflow management.

If the objective is met after processing the work items through a stage of the configured workflow (at 870) then the system may output the results for external applications or consumption by the user (at 880). However, if after an action of the workflow the objective has not been realized, the method may return to the workflow configuration stage (at 840), where the workflow configuration may be revisited now that the previous action has been taken, as previously discussed.

III. System Embodiments

Now that the systems and processes for the workflow management have been described in considerable detail, attention shall be turned toward possible apparatuses for embodying the above disclosed workflow management system. In some embodiments, much of the processing and data manipulation may be driven by configured computer systems. However, due to the specialized nature of healthcare information sources, in some embodiments, interfaces for gaining information from specialized encrypted data stores are required, as well as mechanisms for collecting and storing data from any number of medical instruments.

Figure 15A:
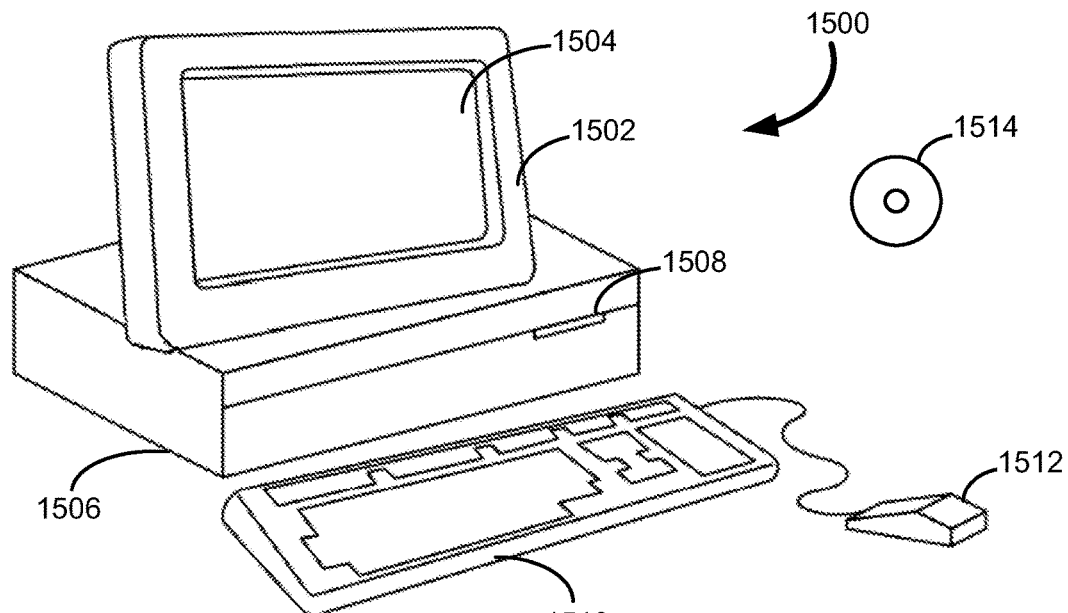
FIGS. 15A and 15B are example illustrations of a computer system capable of embodying the current invention.
Figure 15B:
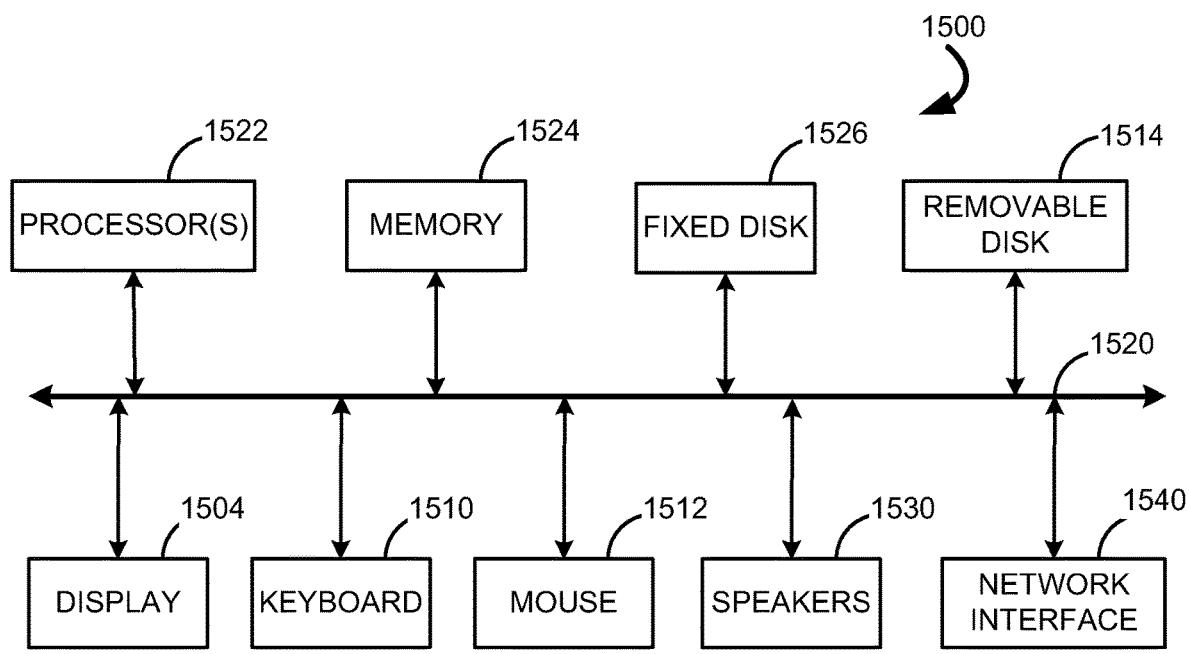

FIGS. 15A and 15B illustrate a Computer System 1500, which is suitable for implementing embodiments of the present invention. FIG. 15A shows one possible physical form of the Computer System 1500. Of course, the Computer System 1500 may have many physical forms ranging from a printed circuit board, an integrated circuit, and a small handheld device up to a huge super computer. Computer system 1500 may include a Monitor 1502, a Display 1504, a Housing 1506, a Disk Drive 1508, a Keyboard 1510, and a Mouse 1512. Disk 1514 is a computer-readable medium used to transfer data to and from Computer System 1500.

FIG. 15B is an example of a block diagram for Computer System 1500. Attached to System Bus 1520 are a wide variety of subsystems. Processor(s) 1522 (also referred to as central processing units, or CPUs) are coupled to storage devices, including Memory 1524. Memory 1524 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A Fixed Disk 1526 may also be coupled bi-directionally to the Processor 1522; it provides additional data storage capacity and may also include any of the computer-readable media described below. Fixed Disk 1526 may be used to store programs, data, and the like and is typically a secondary storage medium (such as a hard disk) that is slower than primary storage. It will be appreciated that the information retained within Fixed Disk 1526 may, in appropriate cases, be incorporated in standard fashion as virtual memory in Memory 1524. Removable Disk 1514 may take the form of any of the computer-readable media described below.

Processor 1522 is also coupled to a variety of input/output devices, such as Display 1504, Keyboard 1510, Mouse 1512 and Speakers 1530. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, motion sensors, brain wave readers, or other computers. Processor 1522 optionally may be coupled to another computer or telecommunications network using Network Interface 1540. With such a Network Interface 1540, it is contemplated that the Processor 1522 might receive information from the network, or might output information to the network in the course of performing the above-described workflow management of medical records. Furthermore, method embodiments of the present invention may execute solely upon Processor 1522 or may execute over a network such as the Internet in conjunction with a remote CPU that shares a portion of the processing.

Software is typically stored in the non-volatile memory and/or the drive unit. Indeed, for large programs, it may not even be possible to store the entire program in the memory. Nevertheless, it should be understood that for software to run, if necessary, it is moved to a computer readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable medium." A processor is considered to be "configured to execute a program" when at least one value associated with the program is stored in a register readable by the processor.

In operation, the computer system 1500 can be controlled by operating system software that includes a file management system, such as a disk operating system. One example of operating system software with associated file management system software is the family of operating systems known as Windows® from Microsoft Corporation of Redmond, Washington, and their associated file management systems. Another example of operating system software with its associated file management system software is the Linux operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is, here and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may, thus, be implemented using a variety of programming languages.

In alternative embodiments, the machine operates as a standalone device or may be connected (e.g., networked) to other machines. In a networked deployment, the machine may operate in the capacity of a server or a client machine in a client-server network environment or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies of the presently disclosed technique and innovation.

In general, the routines executed to implement the embodiments of the disclosure may be implemented as part of an operating system or a specific application, component, program, object, module or sequence of instructions referred to as "computer programs." The computer programs typically comprise one or more instructions set at various times in various memory and storage devices in a computer, and when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

In sum, the present invention provides systems and methods for the efficient management of workflows via bundling of data elements into work items, contextual configuration of the workflows, and routing of the work items through the workflows in a manner that maximizes an objective (energy based routing). Such systems and methods enable the processing of a very large amount of healthcare related data to meet an objective of a user in an efficient manner.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

Any patents and applications and other references noted above, including any that may be listed in accompanying filing papers, are incorporated herein by reference. Aspects of the disclosure can be modified, if necessary, to employ the systems, functions, and concepts of the various references described above to provide yet further embodiments of the disclosure.

What is claimed is:

1. A health information computer system comprising:
at least one memory with instructions stored thereon; and
at least one processor in communication with the at least one memory, wherein the instructions, when executed by the at least one processor, cause the at least one processor to:
receive a plurality of records;
determine a first subset of the plurality of records that include first machine readable objects and a second subset of the plurality of records that include machine unreadable objects;
convert the second subset into an updated second subset including second machine readable objects;
embed information in the first subset and the updated second subset by meta tagging the information into the first subset and the second subset to characterize the first subset and the updated second subset;
extract a plurality of data elements from the first subset and the updated second subset based on the embedded information and a set of similarity rules for determining which data to cluster into a plurality of clusters;
transmit the plurality of data elements to a concept model;
receive a plurality of work items from the concept model; and
route the work items through at least one workflow, wherein work items associated with at least one of higher probability of acceptance or higher reimbursement amounts are routed before work items with at least one of lower probability of acceptance or lower reimbursement amounts in order to achieve a workflow objective of maximizing reimbursement of medical claims.

2. The health information computer system of claim 1, wherein the instructions further cause the at least one processor to convert the second subset into the updated second subset based upon optical character recognition (OCR).

3. The health information computer system of claim 1, wherein the concept model is configured to:
receive the plurality of data elements;
receive a query from a user;
associate, based on the query, each of the plurality of data elements with a respective cluster of the plurality of clusters by utilizing a set of clustering rules, thereby mapping each of the plurality of data elements based on similarities and medical concepts;
apply a set of dynamic time rules to the plurality of data elements, wherein the dynamic time rules represent changes in patient data over time;
dynamically update the set of clustering rules and the set of dynamic time rules;
determine, based on the query, a threshold distance between each of the plurality of data elements and the respective cluster;
determine, based on the mapping and the threshold distance, which data elements of the plurality of data elements satisfy the threshold distance with respect to the respective cluster; and
bundle the data elements that satisfy the threshold distance into a plurality of work items and reject the data elements that do not satisfy the threshold distance.

4. The health information computer system of claim 1, wherein the instructions further cause the at least one processor to:
configure the at least one workflow based on event history for at least one of the work items, current action, or user context;
receive a workflow objective comprising maximizing reimbursement of medical claims; and
determine, for the plurality of work items, a probability that a next action taken in the at least one workflow for at least one work item of the plurality of work items will increase at least one of an acceptance probability for reimbursement or a reimbursement amount.

5. The health information computer system of claim 1, wherein the instructions further cause the at least one processor to route the work items through the at least one workflow in one of an exploration mode or an exploitation mode.

6. The health information computer system of claim 5, wherein the instructions further cause the at least one processor to route the work items in the exploration mode to refine a probabilistic model.

7. The health information computer system of claim 5, wherein the instructions further cause the at least one processor to route the work items in the exploitation mode by comparing an expected outcome for the processing of the work items with respect to an objective and first selecting work items that maximize the objective.

8. At least one non-transitory computer-readable storage medium with instructions stored thereon that, in response to execution by at least one processor, cause the at least one processor to:
at least one memory with instructions stored thereon; and
at least one processor in communication with the at least one memory, wherein the instructions, when executed by the at least one processor, cause the at least one processor to:
receive a plurality of records;

determine a first subset of the plurality of records that include first machine readable objects and a second subset of the plurality of records that include machine unreadable objects;

convert the second subset into an updated second subset including second machine readable objects;

embed information in the first subset and the updated second subset by meta tagging the information into the first subset and the second subset to characterize the first subset and the updated second subset;

extract a plurality of data elements from the first subset and the updated second subset based on the embedded information and a set of similarity rules for determining which data to cluster into a plurality of clusters;

transmit the plurality of data elements to a concept model;

receive a plurality of work items from the concept model; and route the work items through at least one workflow, wherein work items associated with at least one of higher probability of acceptance or higher reimbursement amounts are routed before work items with at least one of lower probability of acceptance or lower reimbursement amounts in order to achieve a workflow objective of maximizing reimbursement of medical claims.

9. The at least one non-transitory computer-readable storage medium of claim 8, wherein the instructions further cause the at least one processor to convert the second subset into the updated second subset based upon optical character recognition (OCR).

10. The at least one non-transitory computer-readable storage medium of claim 8, wherein the concept model is configured to:

receive the plurality of data elements;

receive a query from a user;

associate, based on the query, each of the plurality of data elements with a respective cluster of the plurality of clusters by utilizing a set of clustering rules, thereby mapping each of the plurality of data elements based on similarities and medical concepts;

apply a set of dynamic time rules to the plurality of data elements, wherein the dynamic time rules represent changes in patient data over time;

dynamically update the set of clustering rules and the set of dynamic time rules;

determine, based on the query, a threshold distance between each of the plurality of data elements and the respective cluster;

determine, based on the mapping and the threshold distance, which data elements of the plurality of data elements satisfy the threshold distance with respect to the respective cluster; and bundle the data elements that satisfy the threshold distance into a plurality of work items and reject the data elements that do not satisfy the threshold distance.

11. The at least one non-transitory computer-readable storage medium of claim 8, wherein the instructions further cause the at least one processor to:

configure the at least one workflow based on event history for at least one of the work items, current action, or user context;

receive a workflow objective comprising maximizing reimbursement of medical claims; and determine, for the plurality of work items, a probability that a next action taken in the at least one workflow for at least one work item of the plurality of work items will increase at least one of an acceptance probability for reimbursement or a reimbursement amount.

12. The at least one non-transitory computer-readable storage medium of claim 8, wherein the instructions further cause the at least one processor to route the work items through the at least one workflow in one of an exploration mode or an exploitation mode.

13. The at least one non-transitory computer-readable storage medium of claim 12, wherein the instructions further cause the at least one processor to route the work items in the exploration mode to refine a probabilistic model.

14. The at least one non-transitory computer-readable storage medium of claim 12, wherein the instructions further cause the at least one processor to route the work items in the exploitation mode by comparing an expected outcome for the processing of the work items with respect to an objective and first selecting work items that maximize the objective.

15. A method for health information management implemented by at least one processor in communication with at least one memory, the method comprising:

receiving a plurality of records;

determining a first subset of the plurality of records that include first machine readable objects and a second subset of the plurality of records that include machine unreadable objects;

converting the second subset into an updated second subset including second machine readable objects;

embedding information in the first subset and the updated second subset by meta tagging the information into the first subset and the second subset to characterize the first subset and the updated second subset;

extracting a plurality of data elements from the first subset and the updated second subset based on the embedded information and a set of similarity rules for determining which data to cluster into a plurality of clusters;

transmitting the plurality of data elements to a concept model;

receiving a plurality of work items from the concept model; and routing the work items through at least one workflow, wherein work items associated with at least one of higher probability of acceptance or higher reimbursement amounts are routed before work items with at least one of lower probability of acceptance or lower reimbursement amounts in order to achieve a workflow objective of maximizing reimbursement of medical claims.

16. The method of claim 15, further comprising converting the second subset into the updated second subset based upon optical character recognition (OCR).

17. The method of claim 15, further comprising:

configuring the at least one workflow based on event history for at least one of the work items, current action, or user context;

receiving a workflow objective comprising maximizing reimbursement of medical claims; and determining, for the plurality of work items, a probability that a next action taken in the at least one workflow for at least one work item of the plurality of work items will increase at least one of an acceptance probability for reimbursement or a reimbursement amount.

18. The method of claim 15, further comprising routing the work items through the at least one workflow in one of an exploration mode or an exploitation mode.

19. The method of claim 18, further comprising routing the work items in the exploration mode to refine a probabilistic model.

20. The method of claim 18, further comprising routing the work items in the exploitation mode by comparing an expected outcome for the processing of the work items with respect to an objective and first selecting work items that maximize the objective.

\* \* \* \* \*